(12) United States Patent
Kunnari

(10) Patent No.: US 10,314,815 B2
(45) Date of Patent: Jun. 11, 2019

(54) POLYMORPH OF GRANATICIN B

(71) Applicant: Sloan-Kettering Institute for Cancer Research, New York, NY (US)

(72) Inventor: Tero Kunnari, Aschaffenburg (DE)

(73) Assignee: SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 19 days.

(21) Appl. No.: 15/538,744

(22) PCT Filed: Dec. 22, 2015

(86) PCT No.: PCT/US2015/067399
§ 371 (c)(1),
(2) Date: Jun. 22, 2017

(87) PCT Pub. No.: WO2016/106326
PCT Pub. Date: Jun. 30, 2016

(65) Prior Publication Data
US 2017/0360746 A1   Dec. 21, 2017

Related U.S. Application Data

(60) Provisional application No. 62/095,850, filed on Dec. 23, 2014.

(51) Int. Cl.
*A61K 45/06*   (2006.01)
*A61K 31/122*  (2006.01)
(Continued)

(52) U.S. Cl.
CPC .......... *A61K 31/365* (2013.01); *A61K 31/122* (2013.01); *A61K 45/06* (2013.01); *C07D 493/22* (2013.01); *A61K 2300/00* (2013.01)

(58) Field of Classification Search
CPC .... A61K 31/365; A61K 31/122; A61K 45/06; C07D 493/22
(Continued)

(56) References Cited

U.S. PATENT DOCUMENTS 3,836,642 A   9/1974   Keller et al.
4,270,537 A   6/1981   Romaine
(Continued)

FOREIGN PATENT DOCUMENTS

DE   41 21 468 A1   1/1993
JP   2005-220037 A  8/2005
(Continued)

OTHER PUBLICATIONS

Bachmann et al., Synthesis of the BCD-Ring Substructure of Granaticin A. European J Org Chem. Nov. 2012;2012(33):6562-6569.
(Continued)

*Primary Examiner* — Daniel R Carcanague
(74) *Attorney, Agent, or Firm* — Bryan Cave Leighton Paisner LLP

(57) ABSTRACT

The present invention provides a crystalline Form A of Compound 1, also referred to as Granaticin B, and pharmaceutically compositions thereof. The present invention also provides methods of treating a microbial infection, or a
(Continued)

disease, disorder, or condition associated with abnormal cellular proliferation, using crystalline Form A of Compound 1 or pharmaceutical compositions thereof.

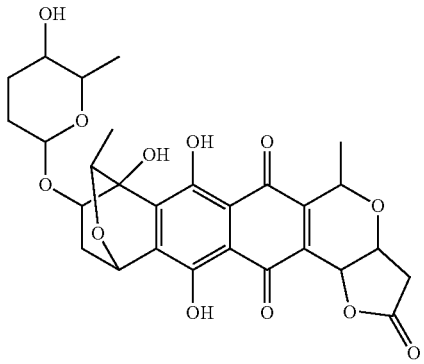

28 Claims, 17 Drawing Sheets

(51) Int. Cl.
    *A61K 31/365*      (2006.01)
    *C07D 493/22*      (2006.01)

(58) Field of Classification Search
    USPC ........................................................ 549/275
    See application file for complete search history.

(56) References Cited

U.S. PATENT DOCUMENTS

| | | | |
|---|---|---|---|
| 4,596,556 A | 6/1986 | Morrow et al. | |
| 4,790,824 A | 12/1988 | Morrow et al. | |
| 4,886,499 A | 12/1989 | Cirelli et al. | |
| 4,940,460 A | 7/1990 | Casey et al. | |
| 4,941,880 A | 7/1990 | Burns | |
| 5,015,235 A | 5/1991 | Crossman | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby | |
| 5,334,144 A | 8/1994 | Alchas et al. | |
| 5,339,163 A | 8/1994 | Homma et al. | |
| 5,383,851 A | 1/1995 | McKinnon et al. | |
| 5,417,662 A | 5/1995 | Hjertman et al. | |
| 5,466,220 A | 11/1995 | Brenneman | |
| 5,480,381 A | 1/1996 | Weston | |
| 5,503,627 A | 4/1996 | McKinnon et al. | |
| 5,520,639 A | 5/1996 | Peterson et al. | |
| 5,527,288 A | 6/1996 | Gross et al. | |
| 5,569,189 A | 10/1996 | Parsons | |
| 5,593,970 A | 1/1997 | Attardo et al. | |
| 5,599,302 A | 2/1997 | Lilley et al. | |
| 5,649,912 A | 7/1997 | Peterson | |
| 5,704,911 A | 1/1998 | Parsons | |
| 5,893,397 A | 4/1999 | Peterson et al. | |
| 5,993,412 A | 11/1999 | Deily et al. | |
| 9,180,105 B2 | 11/2015 | Frattini et al. | |
| 9,492,427 B2 | 11/2016 | Frattini et al. | |
| 9,782,386 B2* | 10/2017 | Frattini | A61K 31/122 |
| 2007/0191330 A1 | 8/2007 | Castillo et al. | |
| 2013/0035301 A1 | 2/2013 | Frattini et al. | |
| 2017/0119731 A1 | 5/2017 | Frattini et al. | |
| 2018/0125815 A1* | 5/2018 | Frattini | A61K 31/122 |

FOREIGN PATENT DOCUMENTS

| | | |
|---|---|---|
| WO | WO 1997/013537 A1 | 4/1997 |
| WO | WO 1997/037705 A1 | 10/1997 |
| WO | WO 1999/034850 A1 | 7/1999 |
| WO | WO 2011/112635 A1 | 9/2011 |

OTHER PUBLICATIONS

Barcza et al., [Metabolic products of microorganisms. 52. Granaticin B]. Helv Chim Acta. Sep. 20, 1966;49(6):1736-40. German.
Bell et al., DNA replication in eukaryotic cells. Annu Rev Biochem. 2002;71:333-74. Epub Nov 9, 2001.
Brown et al., Interaction of the S phase regulator cdc18 with cyclin-dependent kinase in fission yeast. Proc Natl Acad Sci U S A. Jun. 10, 1997;94(12):6142-7.
Chan et al., The role of protein tyrosine kinases and protein tyrosine phosphatases in T cell antigen receptor signal transduction. Annu Rev Immunol. 1994;12:555-92.
Chang et al., Identity of the antitumor antibiotic litmomycin with granaticin A. J Antibiot (Tokyo). Feb. 1975;28(2):156.
Chuang et al., Purification and characterization of the *Schizosaccharomyces pombe* origin recognition complex: interaction with origin DNA and Cdc18 protein. J Biol Chem. May 10, 2002;277(19):16920-7. Epub Feb. 15, 2002.
Dowell et al., Interaction of Dbf4, the Cdc7 protein kinase regulatory subunit, with yeast replication origins in vivo. Science. Aug. 26, 1994;265(5176):1243-6.
Dutta et al., Initiation of DNA replication in eukaryotic cells. Annu Rev Cell Dev Biol. 1997;13:293-332.
Egerer et al., [The effect of potential antineoplastic antibiotics and the metal complex compound cisplatin on in vitro phagocytosis]. Pharmazie. Dec. 1991;46(12):872-4. German.
Elson et al., New Quinone Antibiotics of the Granaticin Type, Isolated from *Streptomyces lateritius*. I. Production, Isolation, and Properties. J. Antibiotics. Apr. 1988;41(4):570-572.
Floss et al., Studies on the biosynthesis of antibiotics. J Nat Prod. Nov.-Dec. 1986;49(6):957-70.
Fluge et al., Gene expression in poorly differentiated papillary thyroid carcinomas. Thyroid. Feb. 2006;16(2):161-75.
Gao et al., A dimeric Smac/diablo peptide directly relieves caspase-3 inhibition by XIAP. Dynamic and cooperative regulation of XIAP by Smac/Diablo. J Biol Chem. Oct. 19, 2007;282(42):30718-27. Epub Aug. 27, 2007.
Gossen et al., A *Drosophila* homolog of the yeast origin recognition complex. Science. Dec. 8, 1995;270(5242):1674-7. Erratum in: Science. Mar. 8, 1996;271(5254):1349.
Gottesman, Mechanisms of cancer drug resistance. Annu Rev Med. 2002;53:615-27.
Hanks et al., Protein kinases 6. The eukaryotic protein kinase superfamily: kinase (catalytic) domain structure and classification. FASEB J. May 1995;9(8):576-96.
Heinstein, Mechanism of action of granaticin: inhibition of ribosomal RNA maturation and cell cycle specificity. J Pharm Sci. Feb. 1982;71(2):197-200.
Hess et al., A human homolog of the yeast CDC7 gene is overexpressed in some tumors and transformed cell lines. Gene. Apr. 28, 1998;211(1):133-40.
Hiratake et al., Treatment of multidrug-resistant murine leukemia with antisense mdr1 oligodeoxynucleotides. Biomed Pharmacother. 1997;51(6-7):276-83.
Hopwood, Genetic Contributions to Understanding Polyketide Synthases. Chem Rev. Nov. 10, 1997;97(7):2465-2498.
Huiqun et al., Practical procedures for genetic manipulation systems for medermycin-producing *Streptomyces* sp. AM-7161. J Basic Microbiol. Jun. 2010;50(3):299-301.
Ichinose et al., Biosynthetic gene clusters of benzoisochromanequinone antibiotics in *Streptomyces* spp.—identification of genes involved in post-PKS tailoring steps. Actinomycetologica. 1998;12:99-109.
Ichinose et al., Cloning, sequencing and heterologous expression of the medermycin biosynthetic gene cluster of *Streptomyces* sp.

(56) References Cited

OTHER PUBLICATIONS

AM-7161: towards comparative analysis of the benzoisochromanequinone gene clusters. Microbiology. Jul. 2003;149(Pt 7):1633-45.
Ichinose et al., Functional complementation of pyran ring formation in actinorhodin biosynthesis in *Streptomyces coelicolor* A3(2) by ketoreductase genes for granaticin biosynthesis. J Bacteriol. May 2001;183(10):3247-50.
Iwashita et al., Signal transduction system for growth factor receptors associated with tyrosine kinase activity: epidermal growth factor receptor signalling and its regulation. Cell Signal. Mar. 1992;4(2):123-32.
Jallepalli et al., Cyclin-dependent kinase and initiation at eukaryotic origins: a replication switch? Curr Opin Cell Biol. Jun. 1997;9(3):358-63.
James et al., The effects of temperature on growth and production of the antibiotic granaticin by a thermotolerant *Streptomycete*. J Gen Microbiol. Jul. 1989;135(7):1997-2003.
Jares et al., Xenopus cdc7 function is dependent on licensing but not on XORC, XCdc6, or CDK activity and is required for XCdc45 loading. Genes Dev. Jun. 15, 2000;14(12):1528-40.
Jiang et al., 6-Deoxy-13-hydroxy-8,11-dione-dihydrogranaticin B, an intermediate in granaticin biosynthesis, from *Streptomyces* sp. CPCC 200532. J Nat Prod. Sep. 26, 2014;77(9):2130-3. doi: 10.1021/np500138k. Epub Aug. 25, 2014.
Johnston et al., First the CDKs, now the DDKs. Trends Cell Biol. Jul. 1999;9(7):249-52.
Keller-Schierlein et al., [The structure of granaticin and of granaticin B. 1. Spectroscopic charcteristics and chemical analysis]. Helv Chim Acta. 1968;51(6):1257-68. German.
Kelly et al., Regulation of chromosome replication. Annu Rev Biochem. 2000;69:829-80.
Krone et al., 13C-NMR and CD Spectroscopy with Isochromanquinones—Potent Methods to Determine the Stereochemistry and the Tautomeric Equilibrium in This Group of Antibiotics. Liebigs Annalen der Chemie. 1987;1987(9):751-58.
Kulanthaivel et al., Novel naphthoquinones from a *Streptomyces* sp. J Antibiot (Tokyo). Mar. 1999;52(3):256-62.
Leatherwood et al., Interaction of Cdc2 and Cdc18 with a fission yeast ORC2-like protein. Nature. Jan. 25, 1996;379(6563):360-3.
Montagnoli et al., Cdc7 inhibition reveals a p53-dependent replication checkpoint that is defective in cancer cells. Cancer Res. Oct. 1, 2004;64(19):7110-6.
Moon et al., Identification and reconstitution of the origin recognition complex from *Schizosaccharomyces pombe*. Proc Natl Acad Sci U S A. Oct. 26, 1999;96(22):12367-72.
Nambiar et al., Identification and functional characterization of ASK/Dbf4, a novel cell survival gene in cutaneous melanoma with prognostic relevance. Carcinogenesis. Dec. 2007;28(12):2501-10. Epub Sep. 3, 2007.
Newton, Protein kinase C: structure, function, and regulation. J Biol Chem. Dec. 1, 1995;270(48):28495-8.
Nomoto et al., Mechanism of action of lactoquinomycin A with special reference to the radical formation. J Antibiot (Tokyo). Aug. 1988;41(8):1124-9.
Nomura et al., Total synthesis of (.+-.)-granaticin. J. Am. Chem Soc. 1987;109(11):3402-3408.
Pham et al., Identification of secondary metabolites from *Streptomyces violaceoruber* TU22 by means of on-flow LC-NMR and LC-DAD-MS. Magn Reson Chem. Sep. 2005;43(9):710-23.
Pines, Cyclins and cyclin-dependent kinases: take your partners. Trends Biochem Sci. Jun. 1993;18(6):195-7.
Poulsen et al., Downregulation of taurine uptake in multidrug resistant Ehrlich ascites tumor cells. Amino Acids. Jun. 2002;22(4):333-50.

Pyrek et al., Naphto- and Anthraquinones of *Streptomyces thermoviolaceus* WR-141. Structures and Model Syntheses. Tetrahedron. 1977;33:673-680.
Rowles et al., Interaction between the origin recognition complex and the replication licensing system in Xenopus. Cell. Oct. 18, 1996;87(2):287-96.
Salaski et al., Pyranonaphthoquinone lactones: a new class of AKT selective kinase inhibitors alkylate a regulatory loop cysteine. J Med Chem. Apr. 23, 2009;52(8):2181-4.
Sclafani, Cdc7p-Dbf4p becomes famous in the cell cycle. J Cell Sci. Jun. 2000;113 ( Pt 12):2111-7.
Sethi, In Vitro Inhibition of Viral DNA Polymerase Activity by Litmomycin. J Pharm Sci. Jan. 1977;66(1):130-2.
Sherr, Cancer cell cycles. Science. Dec. 6, 1996;274(5293):1672-7.
Shimbashi et al., Synthesis of the naphthalene-derived inhibitors against Cdc25A dual-specificity protein phosphatase and their biological activity. Bioorg Med Chem Lett. Jan. 3, 2005;15(1):61-5.
Slebos et al., Gene expression differences associated with human papillomavirus status in head and neck squamous cell carcinoma. Clin Cancer Res. Feb. 1, 2006;12(3 Pt 1):701-9.
Stillman, Cell cycle control of DNA replication. Science. Dec. 6, 1996;274(5293):1659-64.
Sturdík et al., The cytotoxic action of granaticin, a sulfhydryl-reactive antibiotic, on Ehrlich ascites carcinoma cells. Neoplasma. 1983;30(1):3-6.
Tanaka et al., Lactoquinomycin, a novel anticancer antibiotic. I. Taxonomy, isolation and biological activity. J Antibiot (Tokyo). Oct. 1985;38(10):1327-32.
Toral-Barza et al., Discovery of lactoquinomycin and related pyranonaphthoquinones as potent and allosteric inhibitors of AKT/PKB: mechanistic involvement of AKT catalytic activation loop cysteines. Mol Cancer Ther. Nov. 2007;6(11):3028-38. Epub Nov. 7, 2007.
Vashee et al., Assembly of the human origin recognition complex. J Biol Chem. Jul. 13, 2001;276(28):26666-73. Epub Apr. 25, 2001.
Velculescu et al., Analysis of human transcriptomes. Nat Genet. Dec. 1999;23(4):387-8.
Walter, Evidence for sequential action of cdc7 and cdk2 protein kinases during initiation of DNA replication in Xenopus egg extracts. J Biol Chem. Dec. 15, 2000;275(50):39773-8.
Williamson et al., In support of the original medermycin/lactoquinomycin A structure. Org Lett. Dec. 26, 2002;4(26):4659-62.
Yamashita et al., Functional analyses of mouse ASK, an activation subunit for Cdc7 kinase, using conditional ASK knockout ES cells. Genes Cells. Jun. 2005;10(6):551-63.
Extended European Search Report for EP 15874308.8, dated May 29, 2018.
Deng et al., Granaticins and their biosynthetic gene cluster from *Streptomyces vietnamensis*: evidence of horizontal gene transfer. Antonie Van Leeuwenhoek. Nov. 2011;100(4):607-17. doi: 10.1007/s10482-011-9615-9. Epub Jul. 6, 2011.
Snipes et al., Biosynthesis of the antibiotic granaticin. J. Am. Chem. Soc. 1979;101(3):701-706.
Draeger et al., Mechanism of the 2-Deoxygenation Step in the Biosynthesis of the Deoxyhexose Moieties of the Antibiotics Granaticin and Oleandomycin. J. Am. Chem. Soc. 1999;121(11):2611-2612.
Liang et al., Phylogenetic analysis of antibiotic glycosyltransferases. J Mol Evol. Mar. 2007;64(3):342-53. Epub Feb. 26, 2007.
Newsome et al., Nature's palette: the search for natural blue colorants. J Agric Food Chem. Jul. 16, 2014;62(28):6498-511. doi:10.1021/jf501419q. Epub Jul. 8, 2014.
Bernstein, Conventions for naming 1 polymorphs. Jan. 1, 2002. In: Polymorphism in Molecular Crystals. IUCR Monographs on Crystallography. 14. Clarendon Press, Oxford, GB.
Weng Lingling, Clinical Pharmacochemistry. People's Medical Publishing House, pp. 346-348. Aug. 31, 2007.

\* cited by examiner

```
NAME              4apr112.006
EXPNO                      10
PROCNO                      1
Date_                20120425
Time_                   13.13
INSTRUM     AQura_GerNr6329
PROBHD      4 mm MAS BB/1H
PULPROG                cpramp
TD                       4096
SOLVENT                CD2C12
NS                       5067
DS                          0
SWH             45045.047 Hz
FIDRES          10.997326 Hz
AQ              0.0455156 sec
RG                      16384
DW                 11.100 usec
DE                 20.00 usec
TE                   297.5 K
D1             15.00000000 sec ---------- CHANNEL f1 ----------
NUC1                      13C
P15              2000.00 usec
PL1                   4.50 dB
SFO1          100.6228303 MHz ---------- CHANNEL f2 ----------
CPDPRG2                tppm15
NUC2                       1H
P3                  4.40 usec
P31                 6.80 usec
PL2                  -2.00 dB
PL12                 -4.00 dB
SFO2          400.1316005 MHz
SPNAM0                ramp.64
SPOAL0                  0.500
SPOFFS0               0.00 Hz
SI                      16384
SF            100.6129183 MHz
WDW                        EM
SSB                         0
LB                   50.00 Hz
GB                          0
PC                       1.00
SR                  149.28 Hz
```

Figure 7
(Continued)

```
NAME            4apr112.005
EXPNO                    10
PROCNO                    1
Date_              20120423
Time_                 12.12
INSTRUM    AQura_GerNr6329
PROBHD       4 mm MAS BB/1H
PULPROG              cpramp
TD                     4096
SOLVENT              CD2C12
NS                     4780
DS                        0
SWH           45045.047 Hz
FIDRES        10.997326 Hz
AQ             0.0455156 sec
RG                    16384
DW              11.100 usec
DE              20.00 usec
TE                297.1 K
D1          15.00000000 sec ======== CHANNEL f1 ========
NUC1                    13C
P15             2000.00 usec
PL1                 4.50 dB
SFO1         100.6228303 MHz ======== CHANNEL f2 ========
CPDPRG2              tppm15
NUC2                     1H
P3                 4.40 usec
P31                6.80 usec
PL2                -2.00 dB
PL12               -4.00 dB
SFO2         400.1316005 MHz
SPNAM0              ramp.64
SPOAL0                0.500
SPOFFS0             0.00 Hz
SI                    16384
SF           100.6129183 MHz
WDW                      EM
SSB                       0
LB               50.00 Hz
GB                        0
PC                     1.00
SR                149.28 Hz
```

Figure 8
(continued)

```
Version  : PKS_2.01

Title    : MSK777  TK136_19_01 gemörsert

Diffractometer : Transmission
Monochromator  : Curved Germanium (111)
Wavelength     : 1.540598 Cu
Detector       : Image Plate
Scan Mode      : Transmission / Stationary PSD / Fixed omega
Scan Type      : 2Theta ! Raw data file used : E:\Verschiedene\V4560.rmb
! created            : 04-Apr-12 11:56

! Peak search parameters : Expected halfwidth : 0.150
!                          Significance level : 10.0
!                          Peak height level  : 500

Peaklist [ Range 1 : 2Theta =   3.000  79.051 0.015  Imax = 37226 ]
!    D          2Theta    I(rel)   I(abs)    I(int)    FWHM      H  K  L
   17.834480    4.9509    13.97     5124     0.00     0.1800
   10.203506    8.6592    51.74    18971     0.00     0.2100
    9.718068    9.0926   100.00    36665     0.00     0.2250
    8.878934    9.9540    33.26    12194     0.00     0.1500
    7.675597   11.5194    26.33     9654     0.00     0.2250
    7.035887   12.5708    13.00     4766     0.00     0.1800
    6.707521   13.1889    10.60     3887     0.00     0.1500
    5.804516   15.2521    15.85     5813     0.00     0.2250
    5.522740   16.0352    24.90     9131     0.00     0.1800
    5.259232   16.8444    13.89     5092     0.00     0.2100
    5.111773   17.3340    11.20     4107     0.00     0.2100
    4.884393   18.1476    17.20     6305     0.00     0.3300
    4.517023   19.6376     8.79     3223     0.00     0.2250
    4.384967   20.2351     4.30     1577     0.00     0.1800
    4.129109   21.5034     7.82     2869     0.00     0.2700
    4.055562   21.8981    12.54     4599     0.00     0.1800
    3.845650   23.1095    10.76     3946     0.00     0.2700
    3.747940   23.7206     4.63     1698     0.00     0.1500
    3.659094   24.3052     3.49     1281     0.00     0.1950
    3.534577   25.1752     1.53      561     0.00     0.1050
    3.345694   26.6219     3.79     1389     0.00     0.1200
    2.304619   39.0528     1.69      621     0.00     0.1650
```

Figure 12A

```
Title       : MSK777  TK136_19_01 Kristalle

Diffractometer : Transmission
Monochromator  : Curved Germanium (111)
Wavelength     : 1.540598 Cu
Detector       : Image Plate
Scan Mode      : Transmission / Stationary PSD / Fixed omega
Scan Type      : 2Theta ! Raw data file used : E:\Verschiedene\V4560_2.rmb
! created            : 04-Apr-12 12:23

! Peak search parameters : Expected halfwidth : 0.150
!                          Significance level : 10.0
!                          Peak height level  : 500

Peaklist [ Range 1 : 2Theta =  3.000  79.051 0.015  Imax = 62198 ]
!    D         2Theta     I(rel)    I(abs)    I(int)    FWHM      H  K  L 17.893715    4.9345    12.47      7705     0.00     0.1800
   12.458025    7.0899     2.53      1561     0.00     0.3000
   10.205769    8.6572    38.64     23866     0.00     0.2100
    9.717583    9.0931   100.00     61769     0.00     0.2250
    8.871635    9.9622    25.63     15832     0.00     0.1500
    7.674469   11.5211    23.72     14654     0.00     0.2400
    7.035125   12.5722    11.56      7141     0.00     0.1950
    6.715550   13.1731     8.97      5543     0.00     0.2100
    5.801803   15.2593    11.81      7297     0.00     0.2700
    5.520470   16.0419    14.48      8945     0.00     0.1800
    5.256653   16.8527    11.77      7269     0.00     0.2250
    5.116567   17.3176     8.91      5506     0.00     0.1650
    4.867994   18.2092    14.98      9251     0.00     0.2700
    4.515440   19.6445     6.48      4004     0.00     0.2400
    4.381221   20.2526     5.58      3445     0.00     0.2100
    4.223195   21.0188     2.19      1355     0.00     0.1200
    4.128156   21.5084     8.10      5004     0.00     0.1800
    4.057230   21.8890     9.41      5812     0.00     0.2100
    3.849586   23.0855     7.54      4657     0.00     0.3300
    3.743406   23.7497     3.41      2107     0.00     0.1200
    3.657998   24.3126     3.19      1971     0.00     0.1800
    3.341307   26.6575     3.37      2080     0.00     0.1350
    3.077495   28.9906     1.49       918     0.00     0.1200
```

Figure 12B

```
Title       : MSK777  TK136_19_03 gemörsert

Diffractometer  : Transmission
Monochromator   : Curved Germanium (111)
Wavelength      : 1.540598 Cu
Detector        : Image Plate
Scan Mode       : Transmission / Stationary PSD / Fixed omega
Scan Type       : 2Theta ! Raw data file used : E:\Verschiedene\V4561.rmb
! created            : 04-Apr-12 14:26

! Peak search parameters : Expected halfwidth : 0.150
!                          Significance level : 10.0
!                          Peak height level  : 500

Peaklist [ Range 1 : 2Theta =  3.000  79.051 0.015  Imax = 54845 ]
!     D       2Theta    I(rel)   I(abs)   I(int)    FWHM      H  K  L 17.643456   5.0046     5.14     2790     0.00    0.1950
  10.858358   8.1360    11.94     6488     0.00    0.3300
  10.116099   8.7341    42.72    23211     0.00    0.1350
   9.714836   9.0956   100.00    54338     0.00    0.1650
   8.787724  10.0576    26.21    14244     0.00    0.1800
   8.400547  10.5224     2.66     1443     0.00    0.0900
   7.650923  11.5567    25.79    14013     0.00    0.1800
   7.008681  12.6198     9.68     5260     0.00    0.1800
   6.636741  13.3302     9.73     5288     0.00    0.1500
   5.771197  15.3407    13.39     7278     0.00    0.1950
   5.521335  16.0394    22.51    12229     0.00    0.1650
   5.225974  16.9524    11.86     6446     0.00    0.1950
   5.068121  17.4844     8.55     4644     0.00    0.1500
   4.859704  18.2405    20.58    11181     0.00    0.2250
   4.622404  19.1856     2.14     1160     0.00    0.2100
   4.495121  19.7342     8.15     4426     0.00    0.1650
   4.374690  20.2831     5.93     3221     0.00    0.1800
   4.114008  21.5833     3.71     2017     0.00    0.1500
   4.028483  22.0472     7.78     4226     0.00    0.1650
   3.809758  23.3302     8.11     4409     0.00    0.1800
   3.733845  23.8114     2.58     1400     0.00    0.1500
   3.639885  24.4355     2.80     1520     0.00    0.1950
   3.377888  26.3636     2.66     1444     0.00    0.2400
   3.321714  26.8177     2.29     1245     0.00    0.1950
   3.193658  27.9143     2.16     1173     0.00    0.1800
   3.081099  28.9560     1.54      839     0.00    0.1350
   2.882843  30.9956     1.98     1074     0.00    0.1350
   2.306442  39.0207     2.23     1210     0.00    0.0750
```

Figure 13A

```
Title      : MSK777  TK136_19_03 Kristalle

Diffractometer : Transmission
Monochromator  : Curved Germanium (111)
Wavelength     : 1.540598 Cu
Detector       : Image Plate
Scan Mode      : Transmission / Stationary PSD / Fixed omega
Scan Type      : 2Theta ! Raw data file used : E:\Verschiedene\V4561_2.rmb
! created            : 04-Apr-12 13:12

! Peak search parameters : Expected halfwidth : 0.150
!                          Significance level : 10.0
!                          Peak height level  : 500

Peaklist [ Range 1 : 2Theta =  3.000  79.051 0.015  Imax = 53112 ]
!     D         2Theta     I(rel)    I(abs)   I(int)    FWHM      H  K  L 19.461641    4.5368      2.13     1125     0.00    0.1200
    17.644384    5.0043      4.67     2470     0.00    0.2100
    11.211878    7.8791      8.85     4682     0.00    0.3300
    10.102257    8.7461     46.18    24423     0.00    0.1200
     9.718712    9.0920    100.00    52891     0.00    0.1800
     8.799019   10.0446     26.87    14214     0.00    0.2100
     7.639626   11.5739     31.61    16717     0.00    0.1650
     7.000416   12.6348     12.49     6607     0.00    0.1500
     6.647510   13.3085      6.85     3625     0.00    0.2100
     5.987799   14.7826      2.07     1095     0.00    0.0900
     5.763396   15.3616     12.40     6558     0.00    0.1800
     5.517025   16.0520     18.58     9830     0.00    0.1500
     5.217324   16.9807     11.19     5919     0.00    0.2550
     5.067416   17.4869      7.01     3707     0.00    0.1800
     4.855331   18.2571     24.83    13134     0.00    0.2100
     4.487427   19.7684      9.05     4784     0.00    0.1650
     4.370926   20.3008      8.96     4741     0.00    0.2100
     4.118873   21.5575      5.62     2971     0.00    0.1500
     4.026230   22.0597      7.56     3999     0.00    0.1950
     3.807685   23.3431      6.30     3332     0.00    0.1500
     3.729910   23.8369      2.81     1486     0.00    0.1500
     3.635557   24.4650      2.94     1553     0.00    0.1650
     3.497540   25.4463      1.79      946     0.00    0.1200
     3.357976   26.5228      2.72     1440     0.00    0.3300
     3.149010   28.3183      1.67      886     0.00    0.1650
     3.033001   29.4254      2.54     1343     0.00    0.1350
     2.879860   31.0285      1.92     1016     0.00    0.2100
     2.661836   33.6424      1.52      803     0.00    0.1950
```

POLYMORPH OF GRANATICIN B

RELATED APPLICATIONS

The present application is a national stage filing under 35 U.S.C. § 371 of international PCT application, PCT/US2015/067399, filed Dec. 22, 2015, which claims priority under 35 U.S.C. § 119(e) to U.S. provisional patent application, U.S. Ser. No. 62/095,850, filed Dec. 23, 2014, each of which is incorporated herein by reference

BACKGROUND OF THE INVENTION

Granaticins are polyketide-derived antibiotics produced as secondary metabolites by *Streptomyces violaceoruber* (James et al., *J Gen Microbiol.* 1989, 135(7), 1997-2003). Granaticins are benzoisochromanequinones (BIQs; Keller-Schierlein et al. *Helv. Chim. Acta,* 1968, 51, 1257-1268). Chemical modifications of granaticins have been carried out at C-10 via a C—C bond formation either by glycosylation or by dimerization (Hopwood, *Chem Rev.* 1997, 97, 2465-2497; Floss et al., *J Nat Prod.* 1986, 49, 951; Toral-Barza et al, *Mol. Cancer Ther.* 2007, 6, 3028-3038; Salaski et al., *J. Med. Chem.* 2009, 23, 2181-2184). Additional chemical or enzymatic modification can be made to 8,11-Ethanofuro[2,3-e]naphtho[2,3-c:6,7-c']dipyran-2,6,13(9H)-trione, 3,3a,5,8,11,13b-hexahydro-7,8,12,15-tetrahydroxy-5,9-dimethyl-, (3aS,5S,8S,9R,11R,13bS,15R) of the 3-methyl-2-oxabicyclo[2.2.2]oct-5-ene-4,8-diol group of Granaticin A (e.g., coupling a carbohydrate moiety) provides granaticin B (Compound 1 in FIG. 10, also called MSK-777).

In addition to the anti-bacterial activity of granaticins, Frattini et al. has found that granaticins inhibit protein kinase pathways (Change et al., *Antibiot.* 1975, 28, 156; PCT Application Publication WO 2011/112635). In particular, granaticins were found to inhibit Cdc kinase activity based upon hits identified from high-thoroughput screening (HTS) of over 300,000 compounds for their ability to inhibit a heterodimer of a kinase (Cdc7) and an activator (Dbf4) that phosphorylates serine and threonine residues (WO 2011/112635).

Granaticin B was prepared from isolating the culture filtrate of *Streptomyces lateritius* or *Streptomyces violaceoruber* (Elson et al., *J. Antibiotic,* 1988, 41(4), 570-572; U.S. Pat. No. 3,836,642; Barcza et al., *Helv. Chim. Acta,* 1966, 4996), 1736-1740). The current process for preparing granaticin B involves down-stream or chemical unit operation to purify the natural product from fermentation (Keller-Schierlein, *Helv. Chim. Acta.,* 1968, 51, 1257-1268; Gilpin, *J. Antibiot.,* 1988, 41(4), 570-572). This process involves multiple steps including extractions and chromatography. The yield is not desirable, and degradation of the desired product has been observed. Therefore, there is a need to develop feasible a large-scale process for the production of granaticin B for clinical and research purposes.

SUMMARY OF THE INVENTION

A polymorph of granaticin B (Compound 1) has been discovered and named Form A. The present invention provides not only Form A but compositions thereof, which are useful in treating and studying diseases. In certain embodiments, Form A, and pharmaceutical compositions thereof, are useful in treating and/or preventing bacterial infections and/or proliferative diseases (e.g., cancer). Form A is a stable crystalline form of Compound 1. Form A has been characterized by various techniques as described herein including, but not limited to, x-ray powder diffraction, differential scanning calorimetry, and thermogravimetric Fourier-transform infrared thermogram.

Also provided herein are pharmaceutical compositions comprising Form A of Compound 1 and optionally a pharmaceutically acceptable excipient.

The present invention also provides methods of treating a proliferative disease (e.g., cancer) or a bacterial infection using Form A or pharmaceutical compositions thereof.

Also provided herein are methods of preparing the crystalline Form A of Compound 1. In certain embodiments, the methods involve evaporative crystallization from chloroform/methanol or methanol/acetone. The provided methods are useful in preparing crystalline Form A of Compound 1 on a large-scale (e.g. over 50 grams) because the traditional fermentation process would be too voluminous (e.g. over 100 L) for a normal laboratory to handle.

DEFINITIONS

The term "polymorph" refers to a crystalline form of a compound (e.g., Compound 1), or a hydrate or solvate thereof, in a particular crystal packing arrangement. All polymorphs of a particular compound have the same elemental composition. The term "crystalline," as used herein, refers to a solid state form which consists of orderly arrangement of structural units. Different crystalline forms of the same compound, or a hydrate, or solvate thereof, arise from different packing of the molecules in the solid state, which results in different crystal symmetries and/or unit cell parameter. Different crystalline forms usually have different X-ray diffraction patterns, infrared spectra, melting points, densities, hardness, crystal shapes, optical and electrical properties, stabilities, and/or solubility. Recrystallization solvent, rate of crystallization, storage temperature, and other factors may cause one crystalline form to dominate in a particular preparating. Various polymorphs of a compound, or a hydrate or solvate thereof, can be prepared by crystallization under different conditions.

The term "solvate" refers to forms of a compound (e.g., Compound 1) that are associated with a solvent, usually by a solvolysis reaction. This physical association may include hydrogen bonding. Conventional solvents include water, methanol, ethanol, acetic acid, DMSO, THF, diethyl ether, and the like. In certain embodiments, solvates are formed using Class 3 solvents. Categories of solvents are defined in, for example, the International Conference on Harmonization of Technical Requirements for Registration of Pharmaceuticals for Human Use (ICH), "Impurities: Guidelines for Residual Solvents, Q3C(R3), (November 2005). A compound may be prepared, e.g., in crystalline form, and may be solvated. Suitable solvates include pharmaceutically acceptable solvates and further include both stoichiometric solvates and non-stoichiometric solvates. In certain instances, the solvate is capable of isolation, for example, when one or more solvent molecules are incorporated in the crystal lattice of a crystalline solid.

The term "hydrate," refers to a compound (e.g., Compound 1) which is associated with water. Typically, the number of the water molecules contained in a hydrate of a compound is in a definite ratio to the number of the compound molecules in the hydrate. Hydrates include both stoichiometric hydrates and non-stoichiometric hydrates. Therefore, a hydrate of a compound may be represented, for example, by the general formula $R.xH_2O$, wherein R is the organic compound, and x is a number greater than 0. A given compound may form more than one type of hydrate, including, e.g., monohydrates (stoichiometric, x is 1), lower hydrates (non-stoichiometric, x is a number greater than 0 and smaller than 1, e.g., hemihydrates (R.0.5H$_2$O)), and polyhydrates (non-stoichiometric, x is a number greater than 1, e.g., dihydrates (R.2H$_2$O) and hexahydrates (R.6H$_2$O)).

It is also to be understood that compounds that have the same molecular formula but differ in the nature or sequence of bonding of their atoms or the arrangement of their atoms in space are termed "isomers".

As used herein, the term "impurity" refers to extraneous matter included in a compound or composition (e.g., Form A of Compound 1). Extraneous matter includes one or more substances that are different from the compound of interest. In certain embodiments, the extraneous matter is undesired extraneous matter. For example, when an anhydrous compound is desired, the solvent (e.g., water) included with the compound is considered an impurity. When a crystalline compound is desired, an amorphous form of the compound included with the compound is considered an impurity. When a certain polymorph of a compound is desired, a different polymorph of the compound included with the compound is considered an impurity. The term "substantially free of impurities" means that a compound (e.g., Form A of Compound 1), contains no significant amount of extraneous matter (e.g., undesired extraneous matter). In certain embodiments, about 1 wt %, about 2 wt %, about 3 wt %, about 5 wt %, about 7 wt %, or about 10 wt % of extraneous matter in a composition is a significant amount of extraneous matter.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other non-human animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. In certain embodiments, the subject is a non-human animal. In certain embodiments, the animal is human.

The terms "administer," "administering," or "administration," as used herein, refers to implanting, absorbing, ingesting, injecting, inhaling, or otherwise introducing a compound (e.g., Form A of Compound 1) or pharmaceutical composition thereof, in or on a subject. When a compound of the invention is provided in combination with one or more other active agents, "administration" and its variants are each understood to include concurrent and/or sequential introduction of the compound and the other active agents.

As used herein, the terms "condition," "disease," and "disorder" are used interchangeably.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

For example, in certain embodiments, the terms "treatment," "treat," and "treating" refer to administering a medicament (e.g., Form A of Compound 1 or a pharmaceutical composition thereof) in order to reverse, alleviate, delay the onset of, or inhibit the progress of a "pathological condition" (e.g., a disease, disorder, or condition, or one or more signs or symptoms thereof) in a subject. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms. Treatment may also be continued after symptoms have resolved, for example, to delay or prevent recurrence.

The terms "prevention," "prevent," and "preventing," as used herein, refer to administering a medicament (e.g., Form A of Compound 1 or a pharmaceutical composition thereof) beforehand to avert or forestall the appearance of one or more symptoms of a disease or disorder in a subject. The person of ordinary skill in the medical art recognizes that the terms "prevention," "prevent," and "preventing" are not absolute terms. In the medical art these terms are understood to refer to the prophylactic administration of a medicament to substantially diminish the likelihood or seriousness of a condition, or symptom of the condition, and this is the sense intended in this disclosure.

An "effective amount" of a compound described herein refers to an amount sufficient to elicit the desired biological response, e.g., treating or preventing a condition. As will be appreciated by those of ordinary skill in this art, the effective amount of a compound described herein may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer or a bacterial infection, an effective amount of the compound may provide a therapeutic and/or prophylactic benefit in the treatment and/or prevention of the cancer or bacterial infection, or to delay or minimize one or more symptoms associated with the cancer or bacterial infection.

A "therapeutically effective amount" of a compound described herein is an amount sufficient to provide a therapeutic benefit in the treatment of a condition (e.g., cancer or bacterial infection) or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces symptoms or causes of the condition, or enhances the therapeutic efficacy of another therapeutic agent.

A "prophylactically effective amount" of a compound described herein is an amount sufficient to prevent a condition (e.g., cancer or bacterial infection), or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The details of one or more embodiments of the invention are set forth herein. Other features, objects, and advantages of the invention will be apparent from the Detailed Description, the Figures, the Examples, and the Claims.

BRIEF DESCRIPTION OF THE DRAWINGS

FIGS. 12A-12B show the raw XRD data of Form A prepared from the first batch.

FIGS. 13A-13B show the raw XRD data of Form A prepared from the second batch.

DETAILED DESCRIPTION OF CERTAIN EMBODIMENTS

Figure 1:
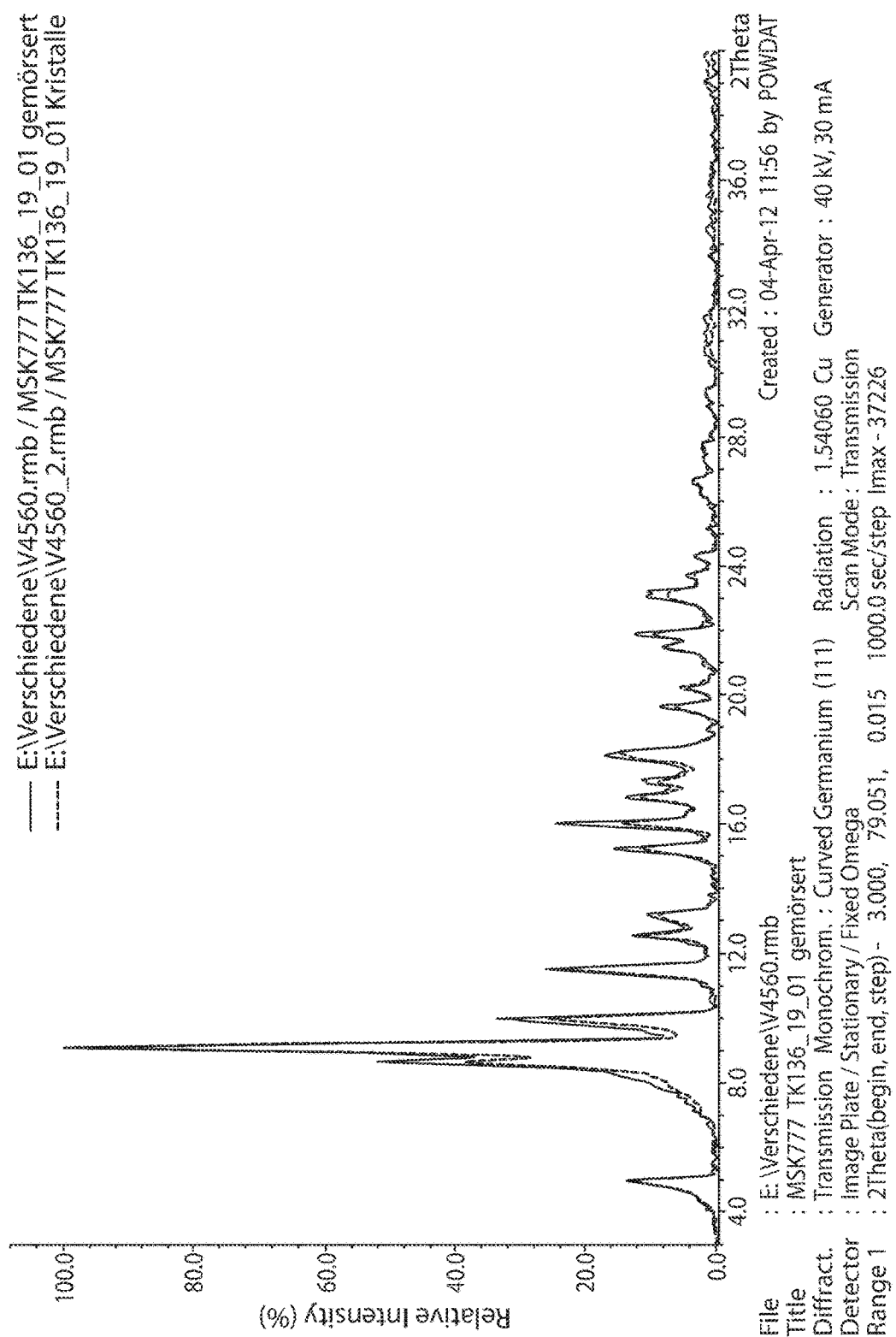
FIG. 1 depicts an X-Ray Powder Diffraction (XRPD) pattern of Form A of Compound 1.

Granaticin B (Compound 1) is a secondary metabolite antibiotic produced by *Streptomyces violaceoruber*. Compound 1 has shown significant potential for the treatment of a variety of disorders including bacterial infections and proliferative diseases. (see, e.g., WO 2011/112635).

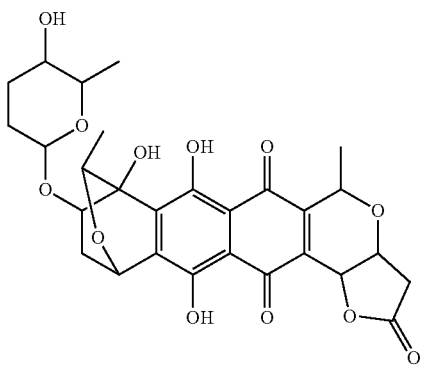

1

Solid Form

A crystalline polymorph of Compound 1 that, as compared to amorphous Compound 1, imparts improved physical characteristics such as stability and/or ease of formulation is desirable. Accordingly, provided herein is a crystalline form (denoted Form A) of Compound 1.

The crystalline Form A of Compound 1 was found to be more stable than amorphous Compound 1. Amorphous Compound 1 is less stable and prone to degradation during the traditional purification process of granaticin B. In some embodiments, the crystalline Form A of Compound 1 demonstrates improved solubility (e.g. higher dissolution rate) compared to the amorphous Compound 1.

In some embodiments, Form A has a water content of about 0.01 wt % to about 5.0 wt %. In some embodiments, Form A has a water content of about 2.0 wt %. Form A is substantially non-hygroscopic.

In some embodiments, Form A is substantially free of impurities. As used herein, impurities include, but are not limited to, any extraneous matter such residual solvents, salts, or other forms of granaticin B. In some embodiments, Form A is 99% free of impurities. In some embodiments, Form A is 97% free of impurities. In some embodiments, Form A is 95% free of impurities. In some embodiments, Form A is 92% free of impurities. In some embodiments, Form A is 90% free of impurities. In certain embodiments, the impurities include extraneous matter, such as a salt forming acid, residual solvents, or any other impurities that may result from the preparation and/or isolation of Compound 1. In some embodiments, Form A is substantially free of amorphous Compound 1. In some embodiments, Form A is substantially free of another crystalline form of Compound 1. In some embodiments, Form A is substantially free of a salt of Compound 1. In some embodiments, Form A is substantially free of a solvate of Compound 1.

Different solid forms of a compound typically differ in their physical and chemical properties based on the arrangement of the molecules in the solid form (e.g., the arrangement of the molecule in the crystal lattice). A given substance may give rise to a variety of solid forms, in particular a variety of crystalline forms, wherein each form has different and distinct physical and chemical properties, such as solubility profiles, thermodynamic and chemical stabilities, melting points, and/or x-ray diffraction peaks.

The crystalline Form A can be characterized by one or more of the characteristics described herein including, but not limited to, XRPD diffraction pattern and/or peaks, DSC thermogram, TG-FTIR thermogram, and/or NMR peaks, appearance, melting point, solubility, and stability. In certain embodiments, the crystalline Form A is characterized by XRPD diffraction pattern and/or peaks. In certain embodiments, the crystalline Form A is characterized by XRPD diffraction pattern and/or peaks, and at least one other technique as described herein (e.g., DSC thermogram, DVS isotherm, or TG-FTIR thermogram).

Figure 2:
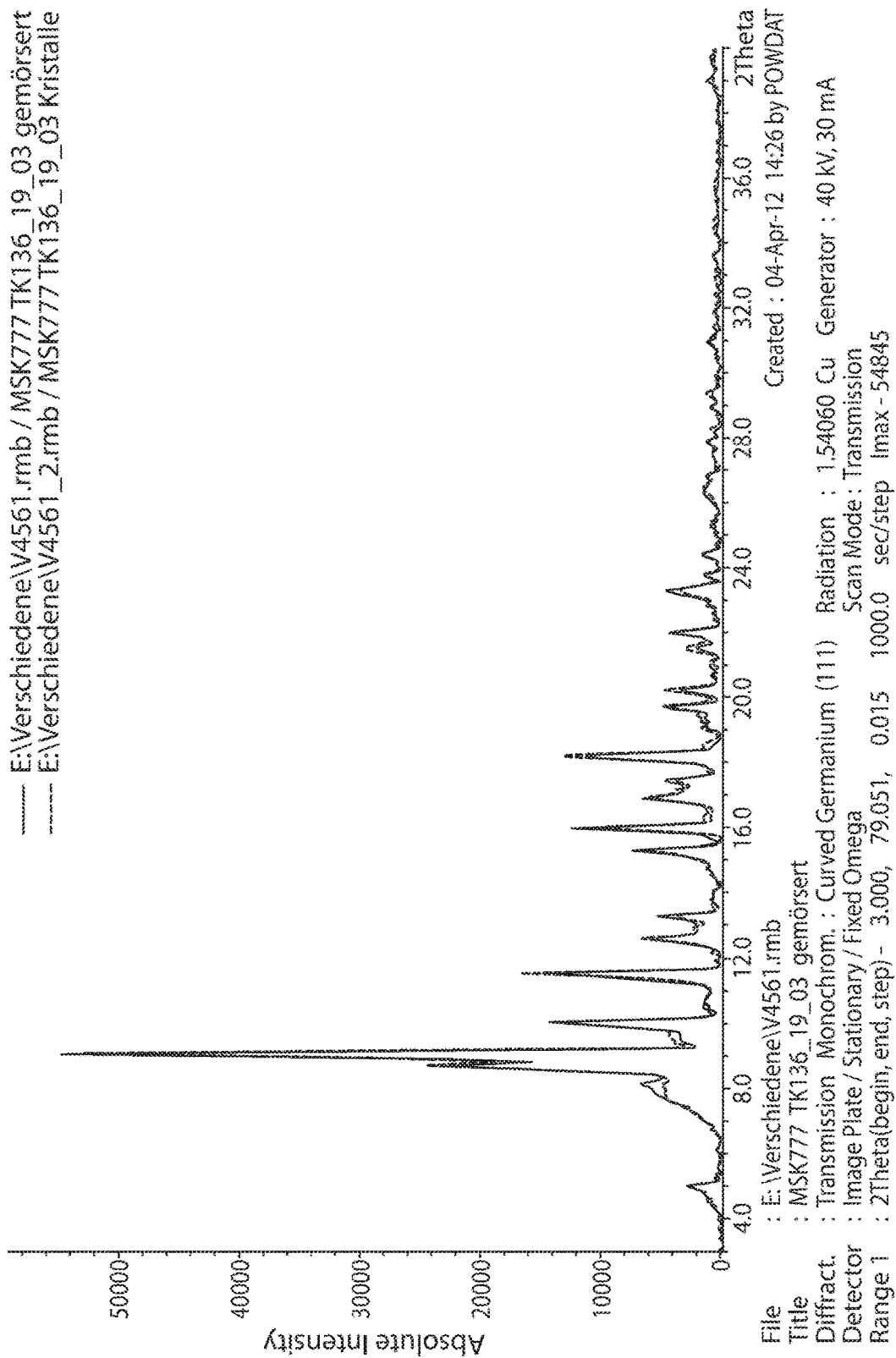
FIG. 2 depicts another XRPD pattern of Form A from another batch.

In some embodiments, the crystalline Form A is characterized by an X-ray powder diffraction pattern substantially similar to the one depicted in FIG. 1. In some embodiments, the crystalline Form A is characterized by an X-ray powder diffraction pattern substantially similar to the one depicted in FIG. 2. In some embodiments, the crystalline Form A is characterized in that it has one or more peaks in its X-ray powder diffraction pattern selected from those in Table 1. In some embodiments, the crystalline Form A is characterized by at least one, at least two, at least three, at least four, at least five, at least six, at least seven, at least eight, at least nine, at least ten, at least eleven, at least twelve, at least thirteen, at least fourteen, at least fifteen, at least sixteen, or at least seventeen peaks in its X-ray powder diffraction pattern selected from those in Table 1. In some embodiments, the crystalline Form A of Compound 1 is characterized in that it has one or more peaks in its X-ray powder diffraction pattern selected from the strong and very strong peaks in Table 1. In some embodiments, the crystalline Form A of Compound 1 is characterized in that it has all the peaks in its X-ray powder diffraction pattern selected from the strong and very strong peaks in Table 1. In some embodiments, the crystalline Form A of Compound 1 is characterized in that it has one or more peaks in its X-ray powder diffraction pattern selected from the very strong peaks in Table 1. In some embodiments, the crystalline Form A of Compound 1 is characterized in that it has all the peaks in its X-ray powder diffraction pattern selected from the very strong peaks in Table 1. In some embodiments, the crystalline Form A of Compound 1 is characterized in that it has both very strong peaks listed in Table 1 (i.e., 19.02 and 23.16 angle theta-2).

TABLE 1

X-ray powder diffraction pattern.

| Intensity % | Angle 2-Theta ° | Intensity (relative) |
|---|---|---|
| 15 | 4.8 ± 0.2 | m |
| 48 | 8.6 ± 0.2 | w |
| 100 | 9.0 ± 0.2 | vs |
| 33 | 9.8 ± 0.2 | s |
| 25 | 11.5 ± 0.2 | s |
| 10 | 12.5 ± 0.2 | m |
| 8 | 13.2 ± 0.2 | w |
| 15 | 15.3 ± 0.2 | m |
| 25 | 16.1 ± 0.2 | s |
| 10 | 16.9 ± 0.2 | m |
| 8 | 17.3 ± 0.2 | w |
| 20 | 18.2 ± 0.2 | s |
| 6 | 19.6 ± 0.2 | w |
| 5 | 20.2 ± 0.2 | w |
| 6 | 21.5 ± 0.2 | w |
| 8 | 21.9 ± 0.2 | w |
| 8 | 23.2 ± 0.2 | w |

The terms used in the tables herein have the following meanings: The term "vs" stands for "very strong." The term "s" stands for "strong." The term "m" stands for "medium." The term "w" stands for "weak."

In some embodiments, the crystalline Form A is characterized by one or more peaks in its X-ray powder diffraction pattern selected from those in Table 2. In some embodiments, the crystalline Form A is characterized by at least one, at least two, at least three, at least four, at least five, at least six, at least seven, at least eight, or at least nine peaks in its X-ray powder diffraction pattern selected from those in Table 2. In some embodiments, the characteristic peaks include the very strong peak indicated in Table 2. In some embodiments, the crystalline Form A is characterized by the very strong peak indicated in Table 2, and at least one, at least two, at least three, or at least four of the other strong peaks in its X-ray powder diffraction pattern selected from those in Table 2.

TABLE 2

Select characteristic peaks from the X-ray powder diffraction pattern.

| Intensity % | Angle 2-Theta ° | Intensity (relative) |
|---|---|---|
| 100 | 9.0 ± 0.2 | vs |
| 33 | 9.8 ± 0.2 | s |
| 25 | 11.5 ± 0.2 | s |
| 25 | 16.1 ± 0.2 | s |
| 20 | 18.2 ± 0.2 | s |

Figure 3:
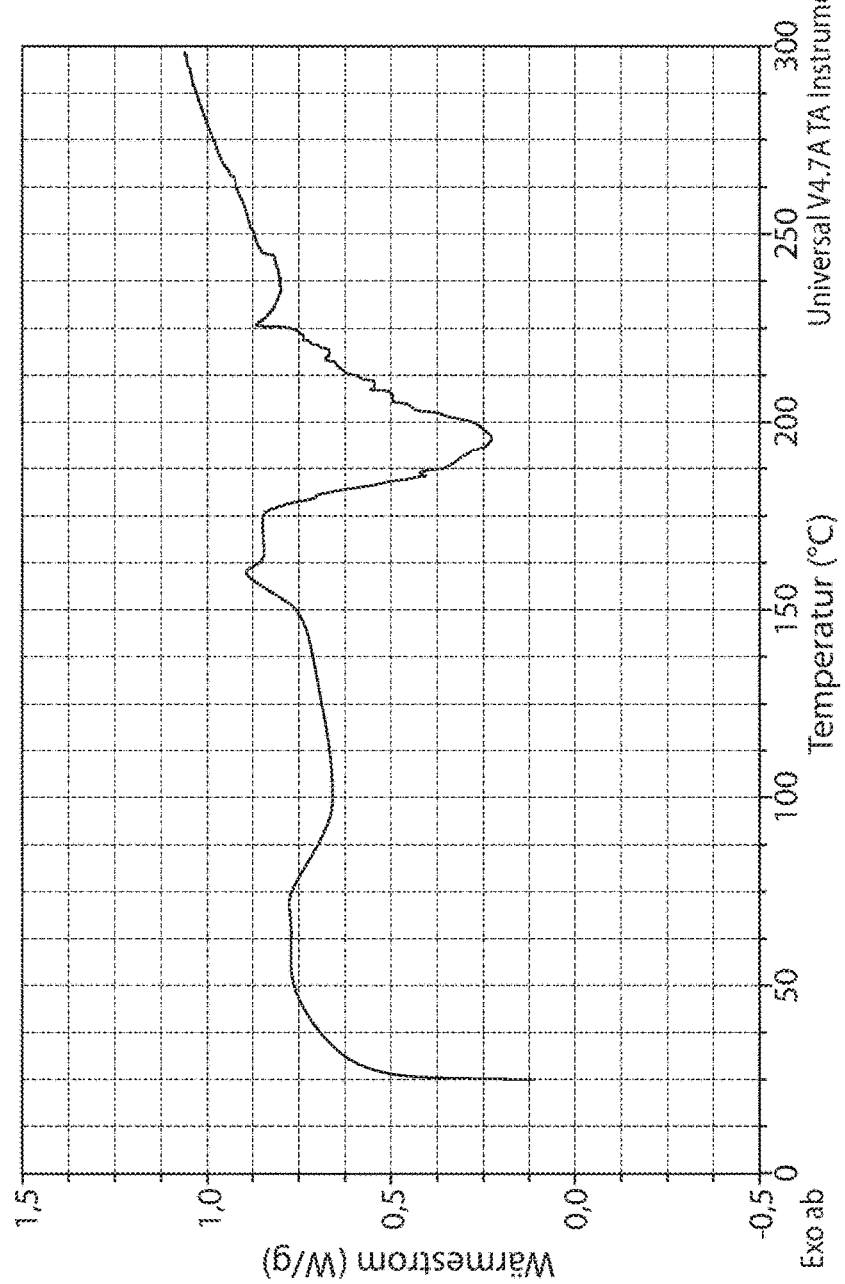
FIG. 3 depicts a Differential Scanning Calorimetry (DSC) thermogram of the Form A.
Figure 4:
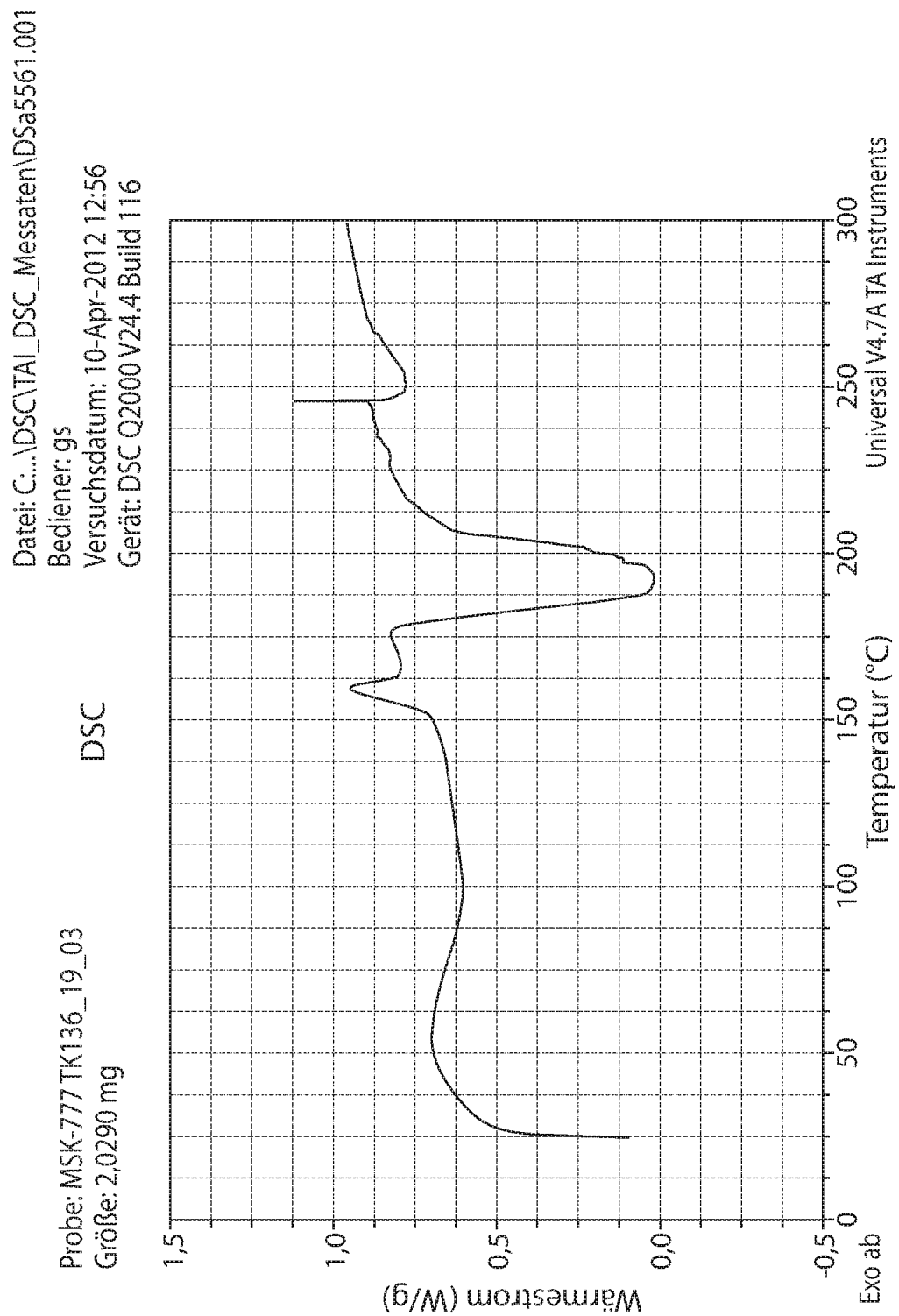
FIG. 4 depicts a DSC thermogram of Form A from another batch.

In some embodiments, the crystalline Form A has a DSC thermogram substantially similar to the one depicted in FIG. 3. In some embodiments, the crystalline Form A has a DSC thermogram substantially similar to the one depicted in FIG. 4. In some embodiments, the crystalline Form A is characterized in that it has a DSC thermogram with an endotherm having a peak temperature ($T_{max}$) of about 190±0.2° C. In some embodiments, the crystalline Form A is characterized by a DSC endothermogram with phase transition in the range of about 140° C. to about 250° C. In some embodiments, the crystalline Form A is characterized by a DSC endothermogram with phase transition in the range of about 155° C. to about 225° C.

Figure 5:
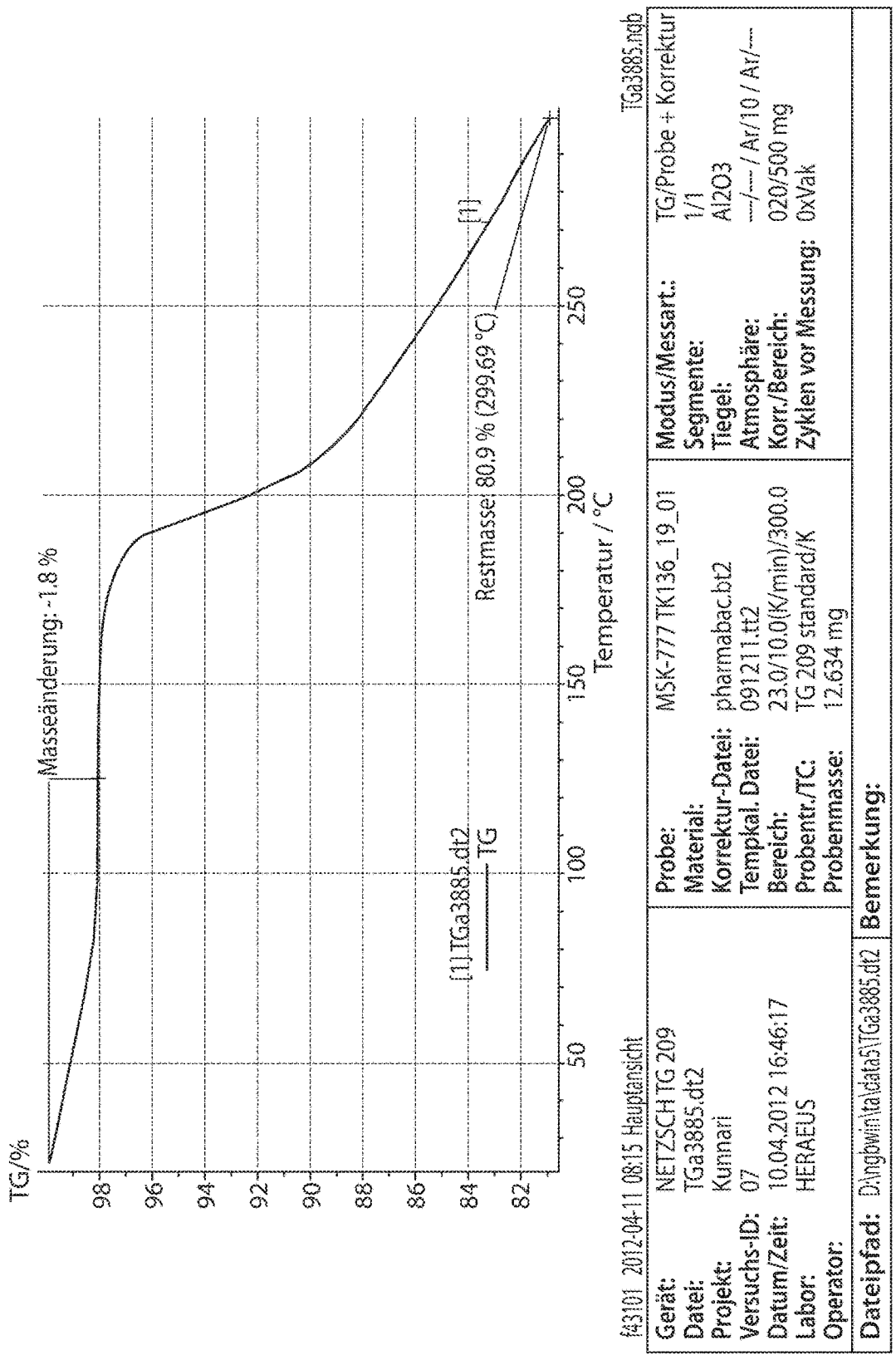
FIG. 5 depicts a Thermogravimetric (TG) thermogram of Form A.
Figure 6:
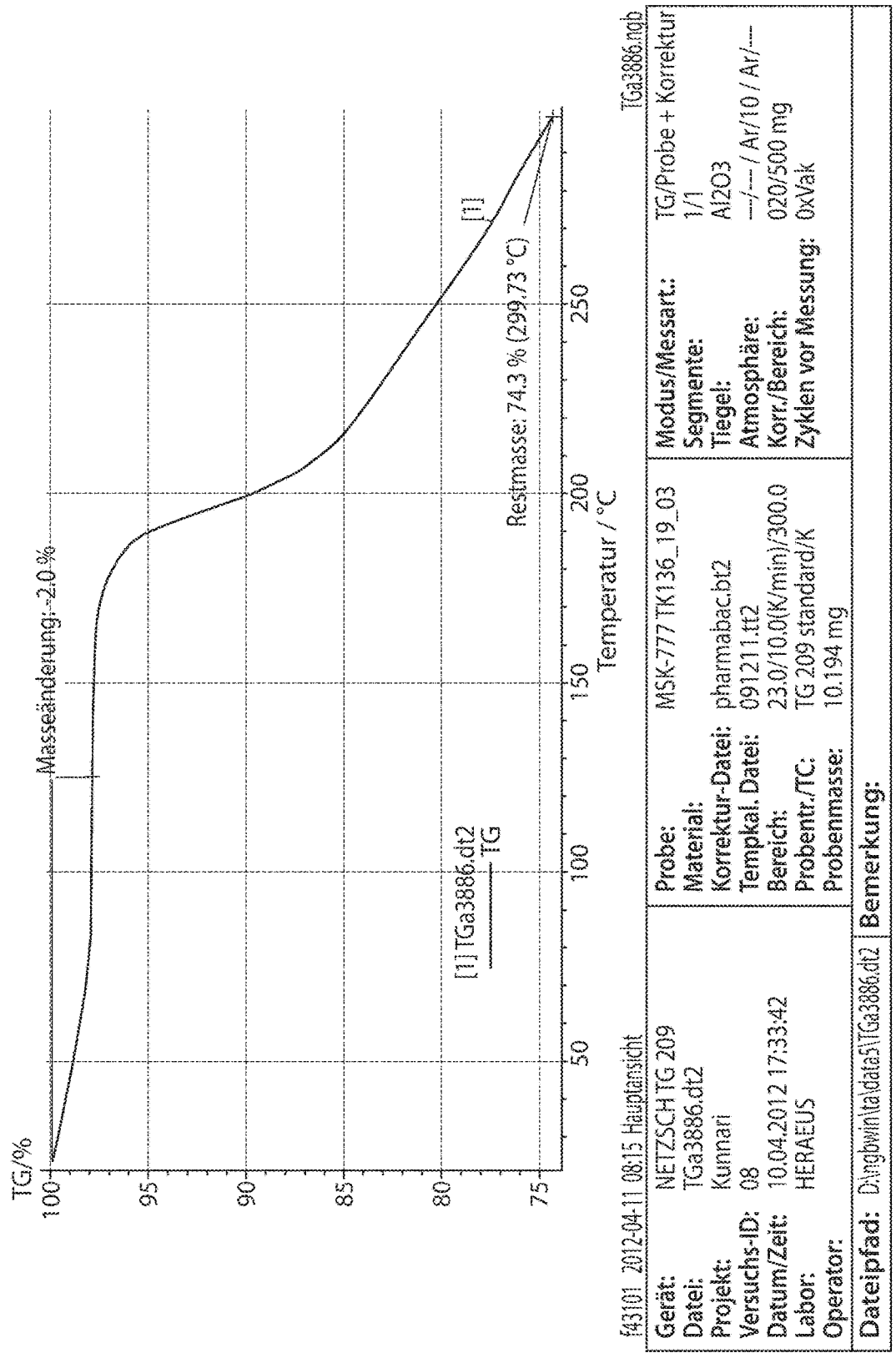
FIG. 6 depicts a TG thermogram of Form A from another batch.

In some embodiments, the crystalline Form A has a TG-FTIR thermogram substantially similar to the one depicted in FIG. 5. In some embodiments, the crystalline Form A has a TG-FTIR thermogram substantially similar to the one depicted in FIG. 6. In some embodiments, the crystalline Form A is characterized in that it losses about 2.0 wt % of $H_2O$ after the temperature of the crystalline Form A is increased from 0° C. to about 150° C. This mass decrease is related to evaporation of water and residual solvent from the crystals. No indication of hydrate(s) is seen due to lack of stepwise reduction of the mass below the melting point.

In some embodiments, the crystalline Form A has an observed decomposition point of about 190±0.2° C.

In some embodiments, the crystalline Form A is stable for at least about 1 month, at least about 2 months, at least about 4 months, at least about 6 months, at least about 12 months, at least about 18 months, at least about 24 months, or at least about 3 years at about 25° C. and about 60% relative humidity. In some embodiments, the crystalline Form A has substantially the same XRPD pattern post storage for at least about 1 month, at least about 2 months, at least about 4 months, at least about 6 months, at least about 12 months, at least about 18 months, at least about 24 months, or at least about 3 years at about 25° C. and about 60% relative humidity.

In some embodiments, the crystalline Form A is stable for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity. In some embodiments, the crystalline Form A has substantially the same XRPD pattern post storage for at least about 1 month, at least about 2 months, at least about 4 months, at least about 6 months, at least about 8 months, at least about 10 months, at least about 12 months, at least about 18 months, or at least about 24 months at about 40° C. and about 75% relative humidity.

Pharmaceutical Compositions

In some embodiments, the present invention provides a composition comprising the crystalline Form A of Compound 1 as described herein and optionally a pharmaceutically acceptable excipient. In certain embodiments, the pharmaceutical compositions are useful for treating a disease, disorder, or condition described herein. In some embodiments, the disease is a bacterial infection. In some embodiments, the disease is a proliferative disease. In some embodiments, a provided composition is formulated for administration to a subject in need of such composition. In certain embodiments, a provided composition is formulated for oral administration to a subject. In certain embodiments, a provided composition is formulated into an oral dosage form. In certain embodiments, a provided composition is formulated into a tablet, powder, pill, capsule, or the like, for oral ingestion by a subject.

Suitable techniques, carriers, and excipients include those found within, for example, *Remington: The Science and Practice of Pharmacy*, 19th edition, Mack Publishing Company, Easton, Pa. 1995; Hoover, John E., *Remington's Pharmaceutical Sciences*, Mack Publishing Company, Easton, Pa. 1975; Liberman, H. A. and Lachman, L., Eds., *Pharmaceutical Dosage Forms*, Marcel Decker, New York, N.Y. 1980; and *Pharmaceutical Dosage Forms and Drug Delivery Systems*, 7$^{th}$ edition, Lippincott Williams & Wilkins, 1999, all of which are incorporated herein by reference in their entireties.

In general, doses of provided pharmaceutical compositions employed for adult human treatment are typically in the range of about 0.01 mg to about 5000 mg per day. In certain embodiments, doses employed for adult human treatment are from about 1 mg to about 1000 mg per day. In certain embodiments, a desired dose is conveniently presented in a single dose or in divided doses administered simultaneously (or over a short period of time) or at appropriate intervals, for example, as two, three, four or more sub-doses per day.

It will be understood that a specific dosage and treatment regimen for any particular subject may depend on a variety of factors, including the activity of the specific compound employed, age, body weight, general health, sex, diet, time of administration, rate of excretion, drug combination, and the judgment of the treating physician and the severity of the particular disease being treated. The amount of a provided compound in the composition may also depend upon the particular compound in the composition.

Methods of Preparing Form A

The present invention also provides methods of preparing the crystalline Form A of Compound 1 as described herein. In certain embodiments, the methods involve evaporative crystallization. In certain embodiments, the methods comprise mixing Compound 1 with chloroform and methanol to provide a mixture. In certain embodiments, the chloroform is water free. In certain embodiments, the solution of Compound 1, chloroform, and methanol is substantially homogeneous. In certain embodiments, the solution of Compound 1, chloroform, and methanol is substantially free of solid materials. In some embodiments, Compound 1 is first dissolved in chloroform (100%) resulting in a solution. Methanol is then added to the solution, and chloroform is removed gradually from the mixture by evaporation. During the evaporation process, methanol is gradually added to the solution. Eventually the crystallization solution contains almost 100% methanol.

In other embodiments, methods of preparing the crystalline Form A of Compound 1 as described herein comprise mixing Compound 1 with methanol and acetone to generate a mixture. In some embodiments, the methods further comprise adding aqueous hydrochloride to acidify the mixture. In some embodiments, the acidified mixture has a water ratio of about 65 vol %. In some embodiments, the concentration of Compound 1 is about 3-6 g/L. In some embodiments, the concentration of Compound 1 is about 4-5 g/L. In certain embodiments, the mixture of Compound 1, methanol, and acetone is substantially homogeneous. In certain embodiments, the mixture of Compound 1, methanol, and acetone is substantially free of solid materials. In some embodiments, Compound 1 is dissolved in acetone (100%) resulting in a solution. Methanol is then added to the solution, and acetone is gradually removed from the mixture by evaporation. During the evaporation process, methanol is gradually added to the solution to reach the target concentration. Eventually the crystallization mixture contains almost 100% methanol.

In certain embodiments, the methods of preparing the crystalline Form A of Compound 1 further comprise lowering the temperature of the mixture to provide a solid. The steps of preparing the crystalline Form A from chloroform and methanol may be performed at any suitable temperature, e.g., a suitable temperature of about −30° C. to about 65° C. Other ranges are also possible. In certain embodiments, the suitable temperature is from about 0° C. to about 30° C. In certain embodiments, the suitable temperature is from about 15° C. to about 25° C. In certain embodiments, the suitable temperature is about 0° C. In certain embodiments, the suitable temperature is about 23° C. (room temperature).

The steps of preparing the crystalline Form A from methanol and acetone may be performed at any suitable temperature, e.g., a suitable temperature of about −30° C. to about 65° C. Other ranges are also possible. In certain embodiments, the suitable temperature is from about 0° C. to about 30° C. In certain embodiments, the suitable temperature is about 0° C. In certain embodiments, the suitable temperature is about 4° C. In certain embodiments, the suitable temperature is about 23° C. (room temperature). In certain embodiments, the steps of preparing the crystalline Form A from methanol and acetone may be performed at one temperature, followed by a lower temperature, followed by a further lower temperature. In certain embodiments, the methods of preparing the crystalline Form A from methanol and acetone comprise stirring the acidified mixture at about 23° C. (room temperature), followed by about 4° C., followed by about 0° C.

In certain embodiments, the methods of preparing the crystalline Form A of Compound 1 further comprise isolating the solid from the mixture.

Compound 1 useful in the preparation of the crystalline Form A may be substantially free of impurities. In certain embodiments, Compound 1 useful in the preparation of the crystalline Form A is about 90% free of impurities. In certain embodiments, Compound 1 useful in the preparation of the crystalline Form A is about 92% free of impurities. In certain embodiments, Compound 1 useful in the preparation of the crystalline Form A is about 95% free of impurities. In certain embodiments, Compound 1 useful in the preparation of the crystalline Form A is about 97% free of impurities. In certain embodiments, Compound 1 useful in the preparation of the crystalline Form A is about 99% free of impurities. In certain embodiments, Compound 1 useful in the preparation of the crystalline Form A is about 99.5% free of impurities. In certain embodiments, Compound 1 useful in the preparation of the crystalline Form A includes a lactone ring opened product as an impurity.

Compound 1 may be present in the solution of Compound 1, chloroform, and methanol at any suitable concentration (e.g., about 0.003 kg/L, about 0.01 kg/L, about 0.02 kg/L, about 0.03 kg/L, about 0.04 kg/L, about 0.05 kg/L, about 0.06 kg/L, about 0.08 kg/L, about 0.1 kg/L, about 0.2 kg/L, about 0.5 kg/L, or about 1 kg/L), as the solubility of Compound 1 permits. In certain embodiments, the concentration of Compound 1 in the solution of Compound 1 and methanol is about 10-100 g/L.

When the mixture of the inventive methods comprises a solid, the solid may be isolated from the mixture by a process known in the art, such as by filtration and/or centrifuge. The solid isolated form the mixture may optionally be subject to a reduced pressure and/or a suitable temperature as described herein. In certain embodiments, the solid in the mixture comprises the crystalline Form A. In certain embodiments, the solid in the mixture comprises the crystalline Form A that is substantially free of impurities. In certain embodiments, the solid isolated from the mixture comprises the crystalline Form A. In certain embodiments, the solid isolated from the mixture comprises the crystalline Form A that is substantially free of impurities. In certain embodiments, the crystalline Form A isolated from the mixture comprises at least 99%, at least 99.2%, at least 99.4%, at least 99.5%, at least 99.6%, at least 99.7%, at least 99.8%, at least 99.9%, at least 99.95%, at least 99.99%, at least 99.995%, or at least 99.999% the crystalline Form A by weight.

In certain embodiments, the mixture is substantially free of solid materials before the temperature of the mixture is lowered. In certain embodiments, the mixture is heterogeneous after the temperature of it is lowered. In certain embodiments, the mixture comprises a solid after the temperature of the mixture is lowered. In certain embodiments, the mixture comprises a solid and a liquid after the temperature of the mixture is lowered.

A suitable condition may also include a suitable pressure under which one or more steps of the inventive methods are performed. In certain embodiments, the suitable pressure is about 1 atmosphere. A suitable pressure may also be higher or lower than 1 atmosphere (i.e., a reduced pressure). A reduced pressure may be a pressure lower than about $10^{-1}$ atmosphere, lower than about $10^{-2}$ atmosphere, lower than about $10^{-3}$ atmosphere, lower than about $10^{-4}$ atmosphere, lower than about $10^{-5}$ atmosphere, lower than about $10^{-6}$ atmosphere, lower than about $10^{-7}$ atmosphere, lower than about $10^{-8}$ atmosphere, lower than about $10^{-9}$ atmosphere, lower than about $10^{-10}$ atmosphere, or lower than about $10^{-11}$ atmosphere.

A suitable condition may also include a suitable atmosphere under which one or more steps of the inventive methods are performed. In certain embodiments, the suitable atmosphere is air. In certain embodiments, the suitable atmosphere is an inert atmosphere. In certain embodiments, the suitable atmosphere is a nitrogen or argon atmosphere.

A suitable condition may also include a suitable time duration that one or more steps of the method lasts. In certain embodiments, the suitable time duration is in the order of minutes (e.g., about 30 min), hours (e.g., about 1 hour, about 2 hours, about 3 hours, about 6 hours, or about 12 hours), days (e.g., about 1 day or about 2 days) or weeks (e.g., about 1 week). For example, in the step of lowering the temperature of the mixture, the temperature of the mixture may be lowered over a suitable time duration described herein.

Treatment Methods

The present invention provides compounds and pharmaceutical compositions useful for inhibiting the growth of or kill rapidly dividing cells comprising administering an effective amount of the Crystalline Form A of Compound 1 as described herein to a subject in need of treatment. In some embodiments, the Crystalline Form A of Compound 1 also contemplates the treatment of a disease, disorder, or condition associated with abnormal cellular proliferation, such as cancer, autoimmune diseases, inflammatory diseases, and diabetic retinopathy.

In one aspect, provided is a method of treating a proliferative disease comprising administering an effective amount of the Crystalline Form A of Compound 1 of the present invention to a subject in need thereof.

Thus, in one aspect, provided is a method of treating cancer comprising administering an effective amount of the Crystalline Form A of Compound 1 of the present invention to a subject in need thereof.

In another aspect, provided is a method of treating an autoimmune disease comprising administering an effective amount of the Crystalline Form A of Compound 1 of the present invention to a subject in need thereof.

In yet another aspect, provided is a method of treating an inflammatory disease comprising administering the Crystalline Form A of Compound 1 of the present invention to a subject in need thereof.

A "proliferative disease" refers to a disease that occurs due to abnormal growth or extension by the multiplication of cells (Walker, Cambridge Dictionary of Biology; Cambridge University Press: Cambridge, UK, 1990). A proliferative disease may be associated with: 1) the pathological proliferation of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune diseases.

The term "angiogenesis" refers to the physiological process through which new blood vessels form from pre-existing vessels. Angiogenesis is distinct from vasculogenesis, which is the de novo formation of endothelial cells from mesoderm cell precursors. The first vessels in a developing embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., excessive or insufficient) angiogenesis that amounts to and/or is associated with a disease.

The terms "neoplasm" and "tumor" are used herein interchangeably and refer to an abnormal mass of tissue wherein the growth of the mass surpasses and is not coordinated with the growth of a normal tissue. A neoplasm or tumor may be "benign" or "malignant," depending on the following characteristics: degree of cellular differentiation (including morphology and functionality), rate of growth, local invasion, and metastasis. A "benign neoplasm" is generally well differentiated, has characteristically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic keratoses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neoplasms." An exemplary pre-malignant neoplasm is a teratoma. In contrast, a "malignant neoplasm" is generally poorly differentiated (anaplasia) and has characteristically rapid growth accompanied by progressive infiltration, invasion, and destruction of the surrounding tissue. Furthermore, a malignant neoplasm generally has the capacity to metastasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases characterized by the development of abnormal cells that proliferate uncontrollably and have the ability to infiltrate and destroy normal body tissues. See, e.g., *Stedman's Medical Dictionary,* 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphoblastic leukemia (ALL) (e.g., B-cell ALL, T-cell ALL), acute myeloid leukemia (AML) (e.g., B-cell AML, T-cell AML), biphenotypic acute leukemia, chronic myeloid leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphomalleukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease)); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic andenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myxosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

As used herein "inhibition," "inhibiting," and "inhibit", refer to the ability of a compound to reduce, slow, halt or prevent activity of a particular biological process in a cell relative to vehicle. In certain embodiments, the biological process is in vitro (e.g., cellular assay). In certain embodiments, the biological process is in vivo.

In certain embodiments, the provided methods for cancer treatment is to treat leukemia, thyroid cancer, melanoma, ovarian cancer, lung cancer, prostate cancer, renal cell carcinoma, cervical cancer, or breast cancer.

In certain embodiments, the leukemia is acute myeloid leukemia, chronic lymphocytic leukemia, acute lymphoblastic leukemia, or biphenotypic acute leukemia.

In another aspect, provided herein is a method of inhibiting cell growth in a subject comprising administering to the subject with a therapeutically effective amount of the crystalline Form A as described herein or a pharmaceutical composition thereof.

In another aspect, provided herein is a method of inhibiting cell growth in a biological sample comprising contacting the biological sample with a therapeutically effective amount of the crystalline Form A as described herein or a pharmaceutical composition thereof.

In another aspect, provided herein is a method of inducing apoptosis of a cell in a subject comprising administering to the subject with a therapeutically effective amount of the crystalline Form A or a pharmaceutical composition thereof.

In another aspect, provided herein is a method of inducing apoptosis of a cell in a biological sample comprising contacting the biological sample with a therapeutically effective amount of the crystalline Form A as described herein or a pharmaceutical composition thereof.

In another aspect, the present invention provides compounds and pharmaceutical compositions useful for treating or preventing microbial infection comprising administering an effective amount of the Crystalline Form A of Compound 1 as described herein to a subject in need of treatment. In some embodiments, the microbial infection is a bacterial infection. In one aspect, the present invention provides methods for inhibiting bacterial growth comprising administering an effective amount of the Crystalline Form A of Compound 1 as described herein to a subject in need of treatment.

In yet another aspect, provided is a method of treating or preventing microbial infection caused by pathogen that are resistant to other treatments, are multi-drug tolerant or resistant and/or that neither grow nor die in the presence of or as a result of other treatments. Such a method can be conducted in vivo (i.e., by administration to a subject) or in vitro (e.g., upon contact with bacteria in a cell culture). For example, in certain embodiments, provided is a method of treating and/or preventing a microbial infection resistant to other treatments comprising administering an effective amount of the Crystalline Form A of Compound 1 to a subject with the microbial infection. In certain embodiments, provided is a method of treating and/or preventing a microbial infection caused by bacteria that are multi-drug resistant, comprising administering an effective amount of the Crystalline Form A of Compound 1 to a subject with the infection. In certain embodiments, the infection-causing bacteria are resistant to other treatments. In some embodiments, the infection-causing bacteria are multi-drug tolerant. In some embodiments, the infection-causing bacteria are multi-drug resistant.

In another aspect, provided herein is a method for inhibiting bacterial cell growth comprising contacting bacteria with the crystalline Form A as described herein, or a pharmaceutical composition thereof. In another aspect, provided herein is a method for inducing bacterial hypersusceptibility comprising contacting bacteria with the crystalline Form A as described herein, or a pharmaceutical composition thereof.

In some embodiments of the provided methods, the bacteria are contacted with the crystalline Form A in vitro. In some embodiments of the provided methods, the bacteria are contacted with the crystalline Form A in vivo.

In some embodiments of the provided methods, the crystalline Form A of Compound 1 is administered with a second therapeutic agent as defined herein. In some embodiments, the second therapeutic agent is an antibiotic.

Exemplary bacterial infections include, but are not limited to, infections with a gram positive bacteria (e.g., of the phylum Actinobacteria, phylum Firmicutes, or phylum Tenericutes); gram negative bacteria (e.g., of the phylum Aquificae, phylum Deinococcus-Thermus, phylum Fibrobacteres/Chlorobi/Bacteroidetes (FCB), phylum Fusobacteria, phylum Gemmatimonadest, phylum Ntrospirae, phylum Planctomycetes/Verrucomicrobia/Chlamydiae (PVC), phylum Proteobacteria, phylum Spirochaetes, or phylum Synergistetes); or other bacteria (e.g., of the phylum Acidobacteria, phylum Chlroflexi, phylum Chrystiogenetes, phylum Cyanobacteria, phylum Deferrubacteres, phylum Dictyoglomi, phylum Thermodesulfobacteria, or phylum Thermotogae).

In certain embodiments, the bacterial infection is an infection with a gram positive bacteria. In certain embodiments, the gram positive bacteria are bacteria of the phylum Firmicutes.

In certain embodiments, the bacteria are a member of the phylum Firmicutes and the genus *Enterococcus*, i.e., the bacterial infection is an *Enterococcus* infection. The term "*Enterococcus* species" refers to a genus of lactic acid bacteria of the phylum Firmicutes. They are Gram-positive cocci which often occur in pairs (diplococci for example *Diplococcus pneumoniae*). Enterococci are facultative anaerobic organisms. Exemplary Enterococci bacteria include, but are not limited to, *E. avium, E. durans, E. faecalis, E. faecium, E. gallinarum, E. solitarius, E. casseliflavus*, and *E. raffinosus*. In certain embodiments, the *Enterococcus* infection is an *E. faecalis* infection. In certain embodiments, the *Enterococcus* infection is an *E. faecium* infection.

In certain embodiments, the bacteria are a member of the phylum Firmicutes and the genus *Staphylococcus*, i.e., the bacterial infection is a *Staphylococcus* infection. The term "*Staphylococcus* species" refers to Gram-positive bacteria, which appear as grape-like clusters when viewed through a microscope and as large, round, golden-yellow colonies, often with .beta.-hemolysis, when grown on blood agar plates. Exemplary Staphylococci bacteria include, but are not limited to, *S. arlettae, S. aureus, S. auricularis, S. capitis, S. caprae, S. carnous, S. chromogenes, S. cohii, S. condimenti, S. croceolyticus, S. delphini, S. devriesei, S. epidermis, S. equorum, S. felis, S. fluroettii, S. gallinarum, S. haemolyticus, S. hominis, S. hyicus, S. intermedius, S. kloosii, S. leei, S. lenus, S. lugdunesis, S. lutrae, S. lyticans, S. massiliensis, S. microti, S. muscae, S. nepalensis, S. pasteuri, S. penttenkoferi, S. piscifermentans, S. psuedointermedius, S. psudolugdensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri*, and *S. xylosus*. In certain embodiments, the *Staphylococcus* infection is an *S. aureus* infection. In certain embodiments, the *Staphylococcus* infection is an *S. epidermis* infection.

In certain embodiments, the bacteria are a member of the phylum Firmicutes and the genus *Streptococcus*, i.e., the bacterial infection is a *Streptococcus* infection. The term "*Streptococcus* species" refers to a genus of spherical, Gram-positive bacteria, and a member of the phylum Firmicutes. Streptococci are lactic acid bacteria. *Streptococcus* species includes bacteria such as, for example, *S. hemolyticus, S. mitis, S. salivarius*, and *S. pneumoniae*. *Streptococcus* species are responsible for infectious diseases such as meningitis, bacterial pneumonia, endocarditis, erysipelas and necrotizing fasciitis ("flesh-eating" microbial infection s).

In certain embodiments, the bacteria are a member of the phylum Firmicutes and the genus *Bacillus*, i.e., the bacterial infection is a *Bacillus* infection. The term "*Bacillus* species" refers to a large number of diverse, rod-shaped Gram positive bacteria that are motile by peritrichous flagella and are aerobic such as *B. anthracis* or *B. subtilis*.

In certain embodiments, the bacteria are a member of the phylum Actinobacteria and the family *Mycobacterium*, i.e., the bacterial infection is a *Mycobacterium* infection. The term "*Mycobacterium* species" refers to Gram-positive, nonmotile, pleomorphic rods related to the *actinomyces*. Tuberculosis in humans is caused by *Mycobacterium tuberculosis*. MDR-TB (multi-drug resistant tuberculosis) describes strains of tuberculosis that are resistant to at least the two first-line TB drugs, isoniazid and rifampicin.

In certain embodiments, the bacterial infection is resistant to other antibiotic therapy. For example, in certain embodiments, the bacterial infection is vancomycin resistant (VR). In certain embodiments, the bacterial infection is a vancomycin-resistant *E. faecalis* infection. In certain embodiments, the bacterial infection is a vancomycin-resistant *E. faecium* infection. In certain embodiments, the bacterial infection is a methicillin-resistant (MR). In certain embodiments, the bacterial infection is a methicillin-resistant *S. aureus* (MRSA) infection.

In certain embodiments, the effective amount is a therapeutically effective amount. In certain embodiments, the effective amount is a prophylactically effective amount. In certain embodiments, the subject is suffering from at least one bacterial infection.

The Crystalline Form A of Compound 1 provided herein is typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The Crystalline Form A of Compound 1 and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of Compound 1 required to achieve an effective amount will vary from subject to subject, depending, for example, on species, age, and general condition of a subject, severity of the side effects or disorder, identity of the mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of Compound 1 for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, Compound 1 and the compositions thereof may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the Crystalline Form A of Compound 1 or composition thereof, as described herein, can be administered in combination with a second therapeutic agent. The Crystalline Form A of Compound 1 or compositions thereof can be administered in combination with a second therapeutic agent to improve bioavailability, reduce and/or modify their metabolism, inhibit their excretion, and/or modify their distribution within the body. It will also be appreciated that the therapy employed may achieve a desired effect for the same disorder, and/or it may achieve different effects.

When "combination therapy" is employed, an effective amount can be achieved using a first amount of Compound 1, or a pharmaceutical composition thereof, and a second amount of an additional suitable therapeutic agent.

In certain embodiments, Compound 1 or a pharmaceutical composition thereof as described herein, and the additional therapeutic agent are each administered in an effective amount (i.e., each in an amount which would be therapeutically effective if administered alone). In other embodiments, Compound 1 or a pharmaceutical composition thereof as described herein, and the additional therapeutic agent are each administered in an amount which alone does not provide a therapeutic effect (a sub-therapeutic dose). In yet other embodiments, Compound 1 or a pharmaceutical composition thereof as described herein can be administered in an effective amount, while the additional therapeutic agent is administered in a sub-therapeutic dose. In still other embodiments, Compound 1 or a pharmaceutical composition thereof as described herein, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of Compound 1 or a pharmaceutical composition thereof as described herein, and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, Compound 1 or a pharmaceutical composition thereof as described herein, and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

The Crystalline Form A of Compound 1 or compositions thereof can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the Crystalline Form A of Compound 1 with the additional therapeutically active agent and/or the desired therapeutic effect to be achieved. In general, it is expected that additional therapeutically active agents utilized in combination do not exceed the levels at which they are utilized individually. In some embodiments, the levels utilized in combination will be lower than those utilized individually.

Exemplary second therapeutic agents include, but are not limited to, antibiotics, anti-viral agents, anesthetics, anti-coagulants, inhibitors of an enzyme, steroidal agents, steroidal or non-steroidal anti-inflammatory agents, antihistamine, immunosuppressant agents, antigens, vaccines, antibodies, decongestant, sedatives, opioids, pain-relieving agents, analgesics, anti-pyretics, hormones, and prostaglandins, etc. Therapeutically active agents include small organic molecules such as drug compounds (e.g., compounds approved by the US Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells.

In certain embodiments, the additional therapeutic agent is an antibiotic. Exemplary antibiotics include, but are not limited to, penicillins (e.g., penicillin, amoxicillin), cephalosporins (e.g., cephalexin), macrolides (e.g., erythromycin, clarithormycin, azithromycin, troleandomycin), fluoroquinolones (e.g., ciprofloxacin, levofloxacin, ofloxacin), sulfonamides (e.g., co-trimoxazole, trimethoprim), tetracyclines (e.g., tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline)), aminoglycosides (e.g., gentamicin, tobramycin, paromomycin), aminocyclitol (e.g., spectinomycin), chloramphenicol, sparsomycin, quinupristin/dalfoprisin (Syndercid™), In some embodiments, the additional therapeutic agent agent is an anti-proliferative agent. In some embodiments, the anti-proliferative agent is an anti-cancer agent. As used herein, the anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, carminomycin, aminopterin, and hexamethyl melamine.

EXAMPLES

In order that the invention described herein may be more fully understood, the following examples are set forth. These examples are for illustrative purposes only and are not to be construed as limiting this invention in any manner.

Example 1

Production of MSK-777

MSK-777 production and purification process consists of following blocks: a) fermentation, b) resin wash and elution, c) concentration, d) RP-chromatography, e) extraction, f) concentration and g) crystallization.

MSK-777 is produced through fermentation of *Streptomyces* strain *Streptomyces violaceoruber*. Fermentation broth contains as product scavenger polymeric absorbent resin XAD7 (The current tradename is XAD7HP, was earlier XAD7). The XAD7 resin is a non-ionic aliphatic acrylic polymer, which traps the formed bacterial metabolites. This direct trapping increases the production rate (inhibiting the feed-back regulation) and prohibits the possible degradation of the already formed metabolites. After fermentation the resin is separated from the fermentation broth with filtration. The resin is selectively washed with small amounts of organic solvent in water, followed by elution of the product with organic solvent or mixture of organic solvent and water.

Figure 11:
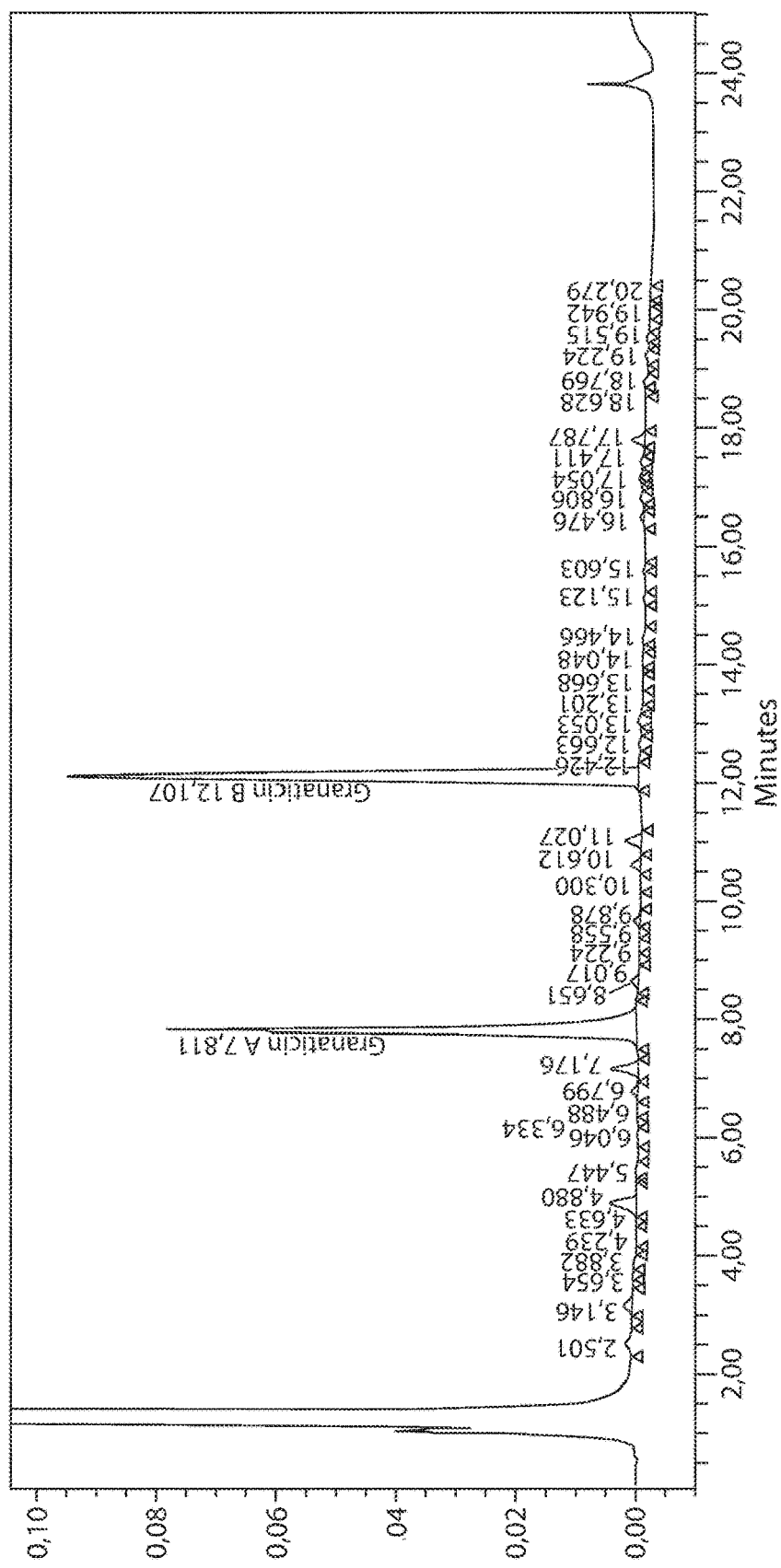
FIG. 11 shows a typical HPLC-profile of the resin extract from fermentation of Compound 1 (see Example 1).

As main metabolites of the fermentation Granaticin A (a biosynthetic precursor of the MSK777) and MSK-777 are detected. Additionally 5-10 minor granaticin group intermediates (side products, degradation products) and several other non-granaticin metabolites are detected. A typical fermentation profile analyzed from the scavenger resin extract consist of 40-60% Granaticin A and 20-40% MSK-777 (see FIG. 11).

The polar impurities of MSK-777 on the scavenger resin are washed with (20:80) acetone-water mixture prior the elution of the desired product. The resin is extracted after the wash sequence with three aliquots of acetone-water (85:15) mixture. The combined eluate fractions are concentrated under vacuum to 20-30% of the original volume. This is necessary to facilitate a fluent loading onto the following reverse preparation (RP) chromatographic system. The pH of the sample before chromatography is in the range of about 5.2 to 7.2. RP-chromatography is performed using Pharmaprep RP-18 (40-63) pm material (Merck). Before injecting the sample, the column is equilibrated with 35% MeOH in water. The column is then loaded with (1-3) wt. % MSK-777 relative to stationary phase weight. Typical loading volumes are (2-4) times the column volume. After loading the column, chromatography is run with a 5-step gradient using increasing MeOH amounts (35/45/50% MeOH) and descending pH (0/0.1% AcH). Pure pooled MSK-777 fractions are combined and extracted with chloroform once using ⅕ of the volume. The chloroform phase is washed twice with 5 g/L $NaHCO_3$ and twice with 0.001% HCl.

The chloroform phase is evaporated to dryness. Dry MeOH is added to solubilize the residue with an final concentration of MSK-777 of about 20-50 g/L. The pH is adjusted with isopropanolic HCl to between 3.5 and 5.0. The formed suspension is filtered, washed quickly with n-pentane, and dried under vacuum for 24 h at room temperature.

Example 2

Preparation of Form A from Chloroform/Methanol (First Batch)

The MSK-777 produced from Example 1 was taken and further dried for 18 h at 45° C. under vacuum (<10 mbar). The batch had been crystallized from water-free chloroform/methanol. The obtained crystals appear as dark-red prisms under the microscope.

Example 3

Preparation of Form A from Methanol/Acetone (Second Batch)

A 5 g of MSK-777 produced from Example 1 was taken and dissolved in methanol-acetone (1:3; v:v). Dilute aqueous hydrochloric acid (pH=4-5) was slowly added under vigorous mixing to the solution until water ratio of ca. 65 vol % was achieved. The final concentration of MSK-777 was about 4-5 g/L. The mixture was stirred two hours at room temperature, followed by four hours at +4° C. and further overnight at 0° C. Crystals were filtered and washed with 15% methanol in water. Crystals were dried first in air, followed by vacuum at ambient temperature and finally at 45° C. and vacuum (<10 mbar). The obtained crystals appear as dark-red prisms.

Example 4

Analysis and Characterization of MSK-777 Before Crystallization 4.1. UV-Spectrum The UV spectrum of MSK-777 shows broad absorptions at 235, 280, 510 and 527 nm. These absorptions indicate a benzoisochromanequinones (BIQ) chromophore. The broad adsorption in the visible region (around 527 nm) is responsible for the intense red color of the substance.

Under basic conditions (pH>8) a bathochromic shift of Vis-absorption (ca. 40 nm) is observed, indicating ionization of slightly acidic phenolic protons. This pH dependent indicatory behavior is characteristic to the BIQ chromophore and is visually observed as the solution turns from red to blue. The color change has an inflection point at ca. pH=8.5 corresponding to the approximate averaged pKa values of the acidic phenol protons.

4.2. Chemical Degradation

MSK-777 shows a slow degradation under acidic conditions (pH<4) at ambient temperature as observed by HPLC. The degradation is caused by hydrolysis of the glycosidic bond, forming Granaticin A, the biosynthetic precursor of MSK-777. Consistently, in a time dependent HPLC experiment a simultaneous increase of Granaticin A chromatographic areas and decrease of Granaticin B areas is observed. The hydrolysis experiment and the almost identical UV spectra indicate that MSK-777 (Granaticin B) and Granatioin A share the same core structure and chromophore. Therefore the structural difference between Granaticin A and MSK-777 arises from a hydrolysable part (sugar moiety) of the latter compound.

4.3. Low Resolution Mass Spectroscopic Analysis

Low resolution mass spectroscopic analysis was conducted using HPLC-MS in electrospray (API) modus. Both, negative and positive ionization modes were recorded simultaneously. Typical for phenolic compounds without a positive ionizable functional group, negative ionization provides a distinct mother ion peak ([M-H]$^-$) together with only a few weak degradation signals. The mother peak with mass of M/z=558 corresponds to the anticipated molecular form of MSK-777 ($C_{28}H_{30}O_{12}$). In contrast, positive ionization shows a complex degradation pattern with a molecular ion obtained by $NH_4^+$ adduct formation ([M+$NH_4^+$) with a mass of 576. The cleavage of the sugar moiety (2-methyltetrahydropyran-3-ol, a loss of m/z 114) from MSK-777 (formation of Granaticin A) was detected in the positive ionization modus, giving a signal with a mass of 445. Similar, the Granaticin A mass spectrum shows the same molecular peak (mass 444, corresponding to the molecular formula of $C_{22}H_{20}O_{10}$) in line with a missing sugar moiety compared to MSK-777.

4.4. High Resolution Mass Spectroscopic Analysis

The high resolution mass spectroscopic analysis shows a molecular mass of 557.16736 ([M-H]$^-$). The difference to the theoretical calculated mass for [M-H]$^-$=$C_{28}H_{29}O_{12}$ is 1.63 ppm. Also the high resolution MS-MS degradation products (two major signals) give the correct anticipated masses. This result confirms theoretical elemental composition of $C_{28}H_{30}O_{12}$.

4.5. IR Spectroscopic Analysis

The FTIR spectrum of MSK-777 shows two strong signals at ca. 1800 and 1600 cm$^{-1}$ due to carbonyl functions. Especially the signal at 1800 cm$^{1}$ is characteristic for quinone carbonyl system The signal at 1600 cm$^{-1}$ arises from the lactone carbonyl. The FTIR spectrum confirms the structure of MSK-777.

4.6. NMR

The data collected from a set of measurements (1D-$^1$H, 1D-sel-TOCSY, 1D-$^{13}$C, 2DCOSY, 2D-HMBC) confirms t the protons and carbons in MSK-777 was made matching the structure of Granaticin B.

Example 5

Analysis and Characterization of Form A 5.1. Analytical Data for Two Batches of Form A

TABLE 3

Analytical Data for Crystalline MSK-777 Batches

| Batch | Purity/ % | Assay/ % | Water/ % | MeOH/ ppm | DCM/ ppm | Pentane/ ppm |
|---|---|---|---|---|---|---|
| TK136_19_01 | 99.35 | 98.96 | 0.86 | 3484 | <46 | <54 |
| TK136_19_03 | 99.41 | 99.97 | 0.97 | 671 | <15 | <54 |

5.2. XRD of Form A

In the X-ray powder diffraction analysis, both batches show sharp and well separated signals indicating crystallinity. Both batches show identical signal pattern, indicating that they share the same crystal structure. The peak positions and their intensities are tabulated in Table 4, below.

TABLE 4

XRPD Peak Positions and Intensities for Investigated MSK-777 Batches

| Batch TK136_19_01 | | Batch TK136_19_03 | |
|---|---|---|---|
| Intensity | 2Θ | Intensity | 2Θ |
| 15 | 4.8 | 5 | 4.8 |
| 4.8 | 8.6 | 42 | 8.6 |
| 100 | 9.0 | 100 | 9.0 |
| 33 | 9.8 | 28 | 10.0 |
| 25 | 11.5 | 25 | 11.5 |
| 10 | 12.5 | 8 | 12.6 |
| 8 | 13.2 | 8 | 13.3 |
| 15 | 15.3 | 13 | 15.4 |
| 25 | 16.1 | 23 | 16.1 |
| 10 | 16.9 | 8 | 16.9 |
| 8 | 17.3 | 6 | 17.3 |
| 20 | 18.2 | 22 | 18.2 |
| 6 | 19.6 | 6 | 19.6 |
| 5 | 20.2 | 5 | 20.2 |
| 6 | 21.5 | 4 | 21.6 |
| 8 | 21.9 | 5 | 22.1 |
| 8 | 23.2 | 5 | 24.2 |

5.3. Thermal Analysis of Form A

The DSC analysis shows for both samples a weak endothermic transition peak at 160° C. followed by a melting/decomposition point at ca. 190° C. The TG analysis shows an approx. 2% decrease in mass in the temperature interval up to the temperature of 100° C. This mass decrease is related to evaporation of water and residual solvent from the crystals. No indication of hydrate(s) is seen (no stepwise reduction of the mass below the melting point). Beyond approx. 185° C. a rapid loss of the mass is detected indicating degradation of the product.

5.4. Solid Phase NMR Analysis of Form A

Both batches show the same solid phase $^{13}C$ NMR spectra. The spectra appear to indicate an amorphous material instead of the expected crystalline phase; broad unresolved signals instead of well separated sharp signals. This result is explained by the observation that during the NMR sample pretreatment consisting of compacting the sample by pressure the initially crystalline material partially melted (i.e. became amorphous).

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. Crystalline Form A of Compound 1:

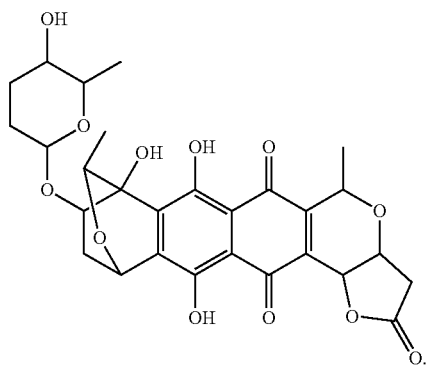

2. The crystalline Form A of claim 1 characterized by an XRPD pattern substantially similar to the one depicted in FIG. 1 or FIG. 2.

3. The crystalline Form A of claim 1 characterized by having in its XRPD pattern at least the four peaks listed in the following table:

| Angle (2-Theta °) |
| --- |
| 9.1 ± 0.2 |
| 10.0 ± 0.2 |
| 11.6 ± 0.2 |
| 16.1 ± 0.2. |

4. The crystalline Form A of claim 1 characterized by having in its XRPD pattern at least the five peaks listed in the following table:

| Angle (2-Theta °) |
| --- |
| 9.1 ± 0.2 |
| 10.0 ± 0.2 |
| 11.6 ± 0.2 |
| 16.1 ± 0.2 |
| 18.3 ± 0.2. |

5. The crystalline Form A of claim 1 characterized by having in its XRPD pattern at least the seven peaks listed in the following table:

| Angle (2-Theta °) |
| --- |
| 9.1 ± 0.2 |
| 10.0 ± 0.2 |

-continued

| Angle (2-Theta °) |
|---|
| 11.6 ± 0.2 |
| 16.1 ± 0.2 |
| 18.3 ± 0.2 |
| 4.5 ± 0.2 |
| 15.4 ± 0.2. |

6. The crystalline Form A of claim 1 characterized by having in its XRPD pattern at least the nine peaks listed in the following table:

| Angle (2-Theta °) |
|---|
| 9.1 ± 0.2 |
| 10.0 ± 0.2 |
| 11.6 ± 0.2 |
| 16.1 ± 0.2 |
| 18.3 ± 0.2 |
| 4.5 ± 0.2 |
| 15.4 ± 0.2 |
| 12.6 ± 0.2 |
| 17.0 ± 0.2. |

7. The crystalline Form A of claim 1 characterized by having in its XRPD pattern at least the thirteen peaks listed in the following table:

| Angle (2-Theta °) |
|---|
| 9.1 ± 0.2 |
| 10.0 ± 0.2 |
| 11.6 ± 0.2 |
| 16.1 ± 0.2 |
| 18.3 ± 0.2 |
| 4.5 ± 0.2 |
| 15.4 ± 0.2 |
| 12.6 ± 0.2 |
| 17.0 ± 0.2 |
| 13.3 ± 0.2 |
| 17.5 ± 0.2 |
| 21.6 ± 0.2 |
| 23.3 ± 0.2. |

8. The crystalline Form A of claim 1 characterized by a DSC endothermogram substantially similar to the one depicted in FIG. 3 or FIG. 4.

9. The crystalline Form A of claim 1 characterized by a DSC endothermogram with a peak temperature ($T_{max}$) of about 190° C.

10. The crystalline Form A of claim 1 characterized by a DSC endothermogram with phase transition in the range of about 140° C. to about 250° C.

11. The crystalline Form A of claim 1 characterized by a thermogravimetric spectrum substantially similar to the one depicted in FIG. 5 or FIG. 6.

Figure 7:
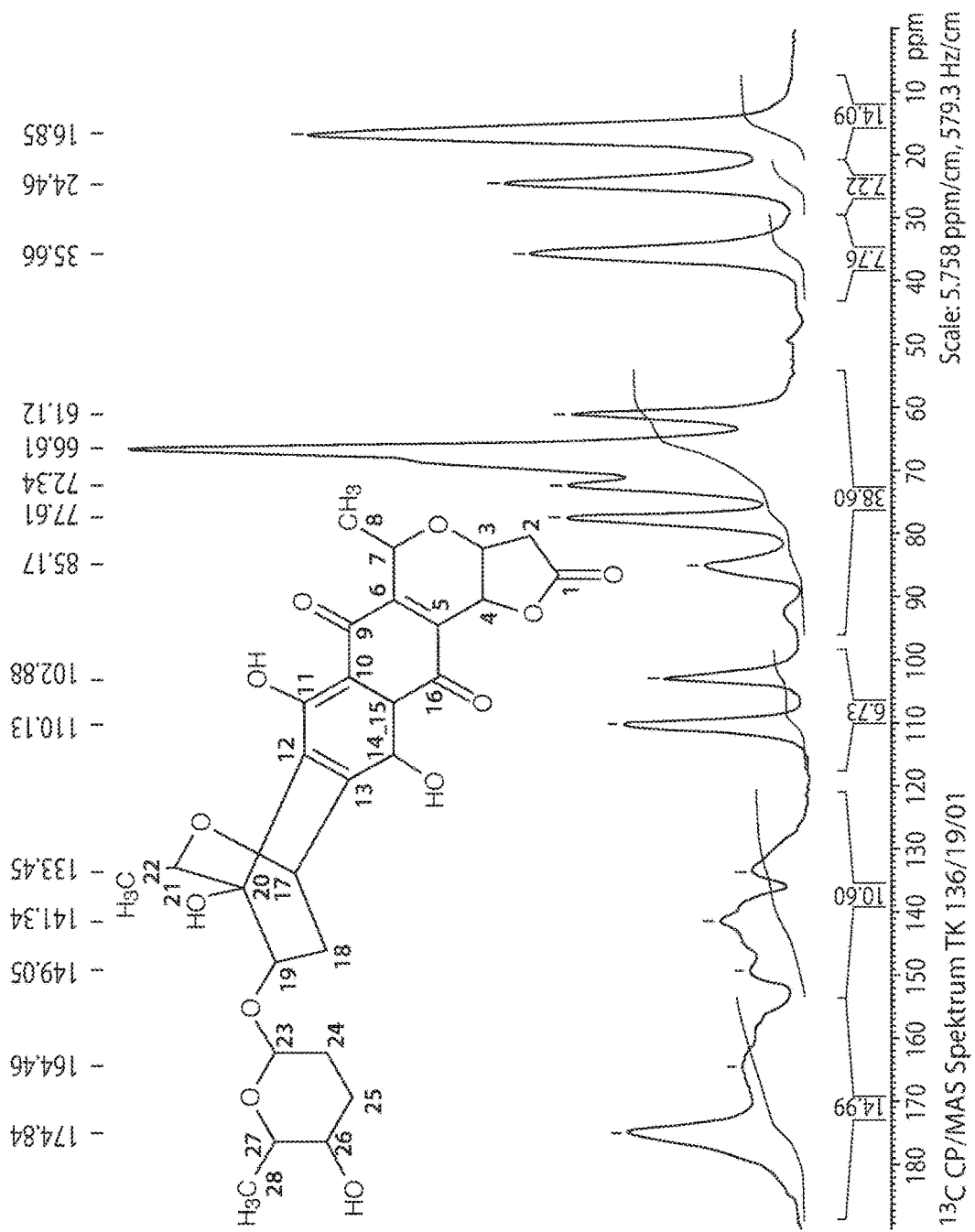
FIG. 7 depicts a Solid-state Cross-Polarization Magic Angle Spinning Carbon-13 Nuclear Magnetic Resonance ($^{13}$C CP/MAS-NMR) spectrum of Form A.
Figure 8:
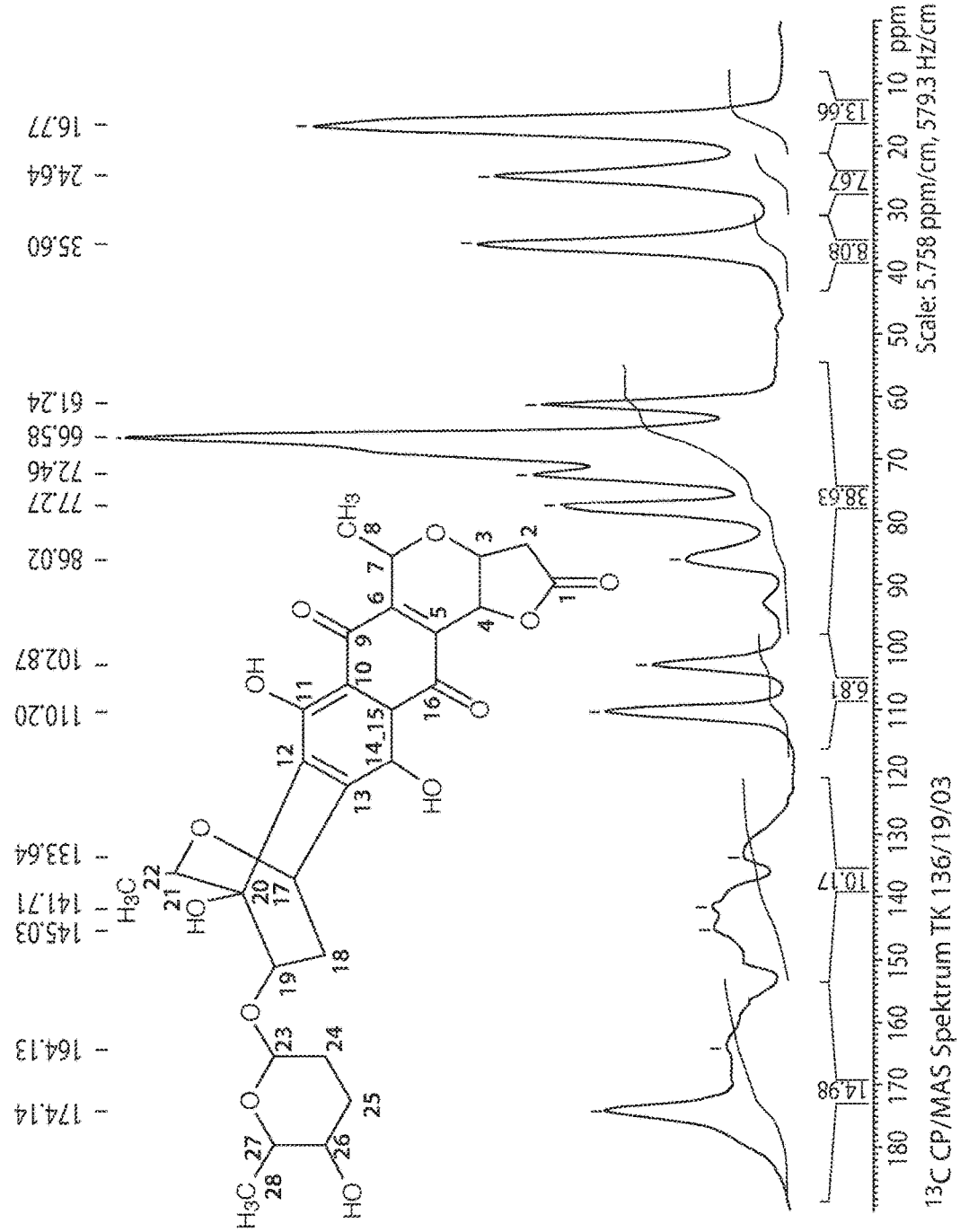
FIG. 8 depicts a $^{13}$C CP/MAS-NMR spectrum of Form A from another batch.
Figure 9:
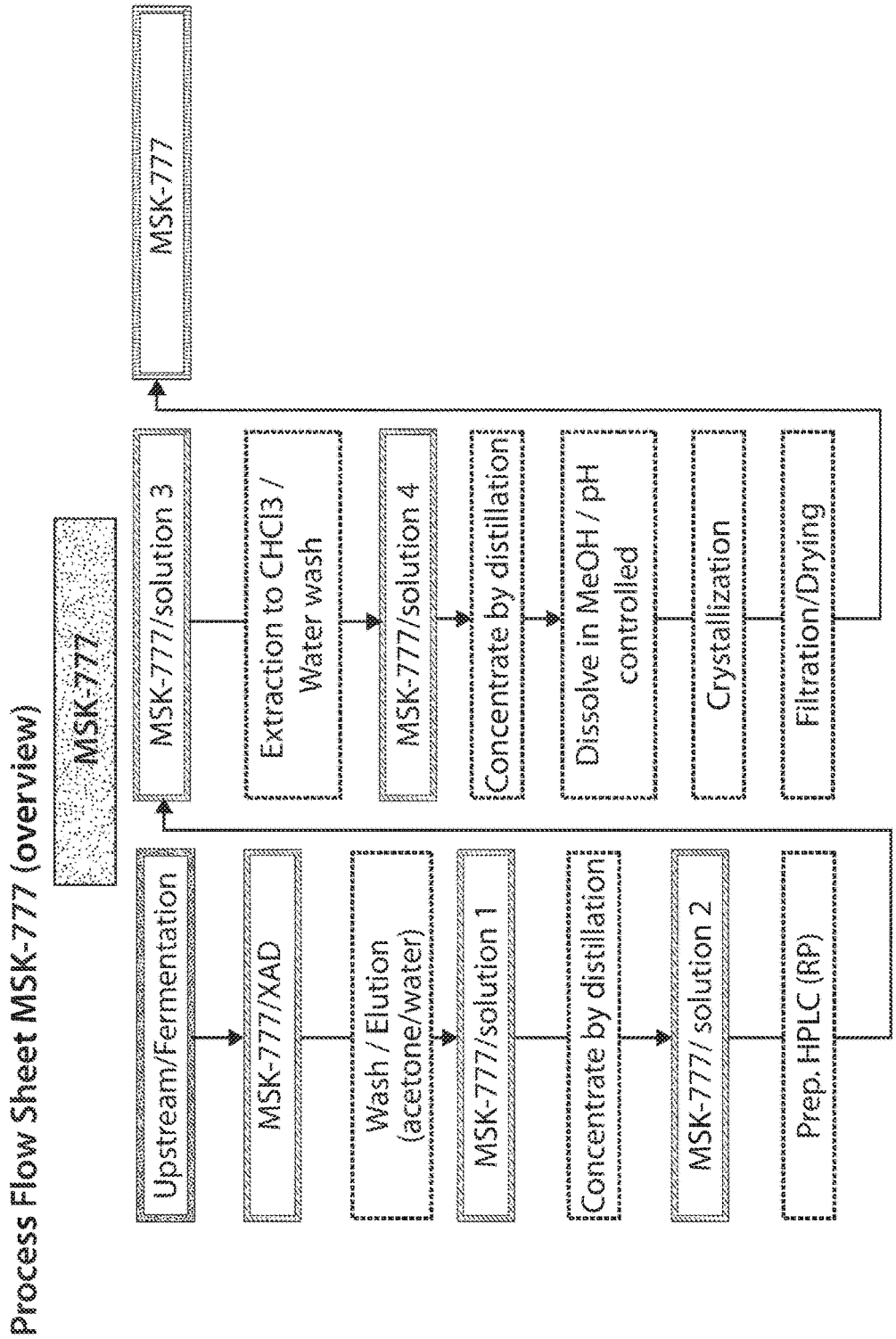
FIG. 9 depicts an exemplary process for producing Form A of Compound 1 (i.e. MSK-777).
Figure 10:
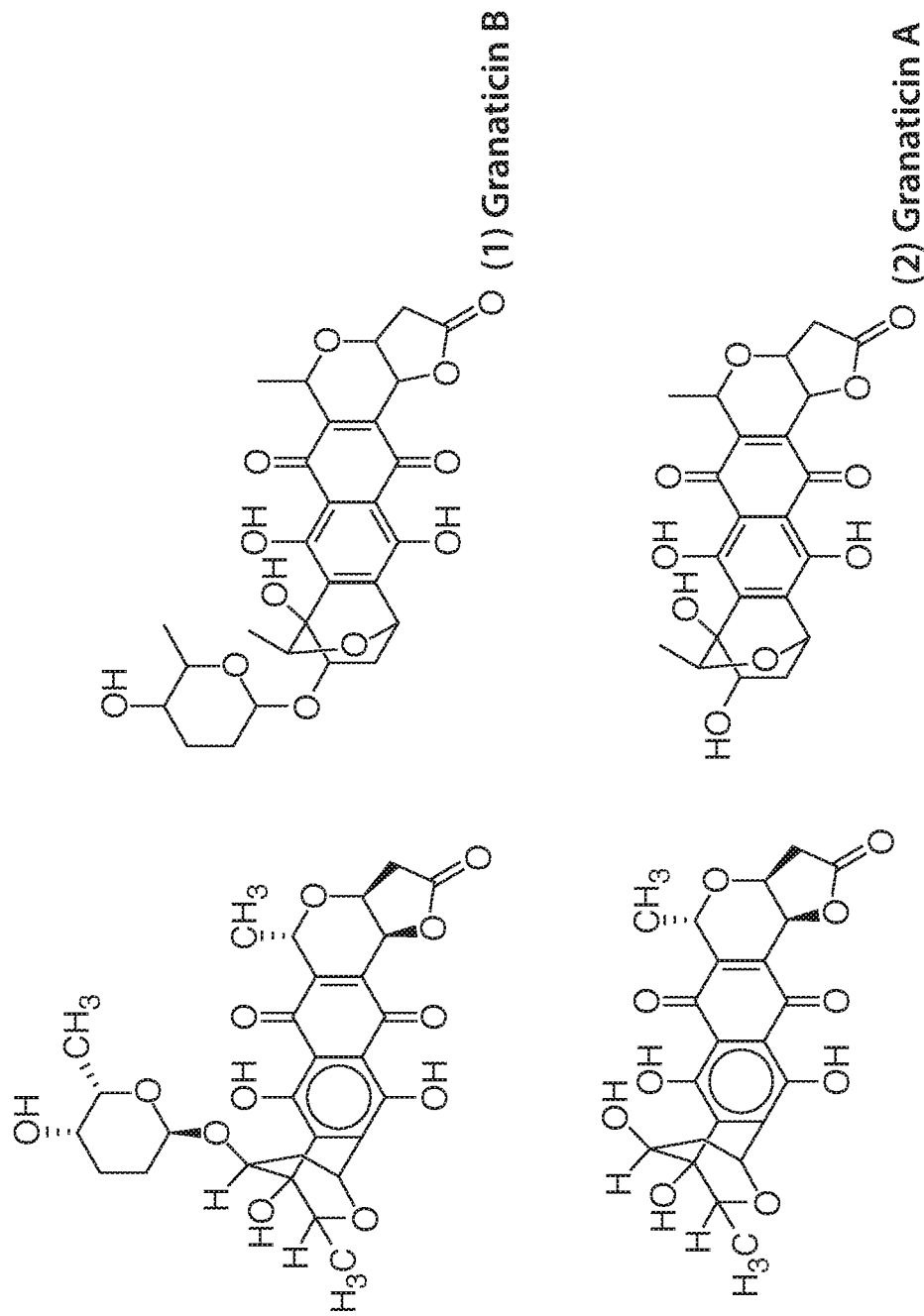
FIG. 10 depicts the structures (flat and stereochemical depictions) of Compound 1 (MSK-777, Granaticin B) and Compound 2 (Granaticin A).

12. The crystalline Form A of claim 1 characterized by an NMR spectrum substantially similar to the one depicted in FIG. 7 or FIG. 8.

13. The crystalline Form A of claim 1, wherein the crystalline Form A is obtained from chloroform and methanol or is obtained from methanol and acetone.

14. A method of preparing the crystalline Form A of claim 1 comprising crystalizing Compound 1 from chloroform and methanol.

15. A method of preparing the crystalline Form A of claim 1 comprising mixing Compound 1 with methanol and acetone to generate a mixture.

16. A pharmaceutical composition comprising crystalline Form A of claim 1 and optionally a pharmaceutically acceptable excipient.

17. A method for treating cancer comprising administering to a subject in need thereof a therapeutically effective amount of crystalline Form A of claim 1.

18. A method of inhibiting cell growth in a subject, the method comprising administering to the subject a therapeutically effective amount of crystalline Form A of claim 1.

19. A method of inducing apoptosis of a cell in a subject, the method comprising:
administering to the subject a therapeutically effective amount of crystalline Form A of claim 1.

20. A method of treating a bacterial infection in a subject comprising administering an effective amount of crystalline Form A of claim 1 to the subject.

21. The crystalline Form A of claim 1 characterized by having in its XRPD pattern at least the seventeen peaks listed in the following table:

| Angle (2-Theta °) |
|---|
| 9.1 ± 0.2 |
| 10.0 ± 0.2 |
| 11.6 ± 0.2 |
| 16.1 ± 0.2 |
| 18.3 ± 0.2 |
| 4.5 ± 0.2 |
| 15.4 ± 0.2 |
| 12.6 ± 0.2 |
| 17.0 ± 0.2 |
| 13.3 ± 0.2 |
| 17.5 ± 0.2 |
| 22.1 ± 0.2 |
| 23.3 ± 0.2 |
| 8.7 ± 0.2 |
| 19.7 ± 0.2 |
| 20.3 ± 0.2 |
| 21.6 ± 0.2. |

22. The crystalline Form A of claim 1, wherein the crystalline Form A is substantially free of amorphous Compound 1.

23. The crystalline Form A of claim 1, wherein about 0.01 wt % to about 10 wt % of amorphous Compound 1 is present.

24. The crystalline Form A of claim 1, wherein about 0.01 wt % to about 5.0 wt % of water is present.

25. The crystalline Form A of claim 1, wherein the crystalline Form A is substantially free of impurities.

26. The method of claim 17, wherein the cancer is leukemia, lymphoma, myelodysplastic syndrome, thyroid cancer, ovarian cancer, lung cancer, prostate cancer, testicular cancer, renal cell carcinoma, liver cancer, colorectal cancer, gastric cancer, pancreatic cancer, bladder cancer, urethral cancer, biliary cancer, gall bladder cancer, cervical cancer, endometrial cancer, breast cancer, head and neck cancer, oral cancer, esophageal cancer, skin cancer, bone cancer, muscle cancer, brain cancer, or ocular cancer.

27. The method of claim 20, wherein the bacterial infection is caused by a gram positive bacterium.

28. The method of claim 27, wherein the gram positive bacterium is of the genus *Staphylococcus, Streptococcus, Micrococcus, Peptococcus, Peptostreptococcus, Enterococcus, Bacillus, Clostridium, Lactobacillus, Listeria, Erysipelothrix, Propionibacterium, Eubacterium,* or *Corynebacterium*.

* * * * *